United States Patent [19]
Palcic et al.

[11] Patent Number: 6,026,174
[45] Date of Patent: Feb. 15, 2000

[54] SYSTEM AND METHOD FOR AUTOMATICALLY DETECTING MALIGNANT CELLS AND CELLS HAVING MALIGNANCY-ASSOCIATED CHANGES

[75] Inventors: Branko Palcic; Calum Eric MacAulay; S. Alan Harrison; Stephen Lam, all of Vancouver; Peter William Payne, Surrey; David Michael Garner, Vancouver; Alexei Doudkine, Delta, all of Canada

[73] Assignee: AccuMed International, Inc., Chicago, Ill.

[21] Appl. No.: 08/907,532

[22] Filed: Aug. 8, 1997

Related U.S. Application Data

[63] Continuation-in-part of application No. 08/888,434, Jul. 7, 1997, Pat. No. 5,942,410, which is a continuation-in-part of application No. 08/644,893, May 10, 1996, Pat. No. 5,889,881, which is a continuation-in-part of application No. 08/425,257, Apr. 17, 1995, abandoned, which is a continuation-in-part of application No. 08/182,453, Jan. 10, 1994, abandoned, which is a continuation-in-part of application No. 07/961,596, Oct. 14, 1992, abandoned.

[51] Int. Cl.[7] .................................................. G06K 9/00
[52] U.S. Cl. ............................................ 382/133; 382/128
[58] Field of Search .................................... 382/133, 128, 382/129, 134; 364/413.1, 413.01; 128/632

[56] References Cited

U.S. PATENT DOCUMENTS

| | | | |
|---|---|---|---|
| 3,857,033 | 12/1974 | Cobb | 435/35 |
| 4,362,386 | 12/1982 | Matsushita et al. | 377/10 |
| 4,453,266 | 6/1984 | Bacus | 382/134 |
| 4,513,438 | 4/1985 | Graham et al. | 382/134 |
| 4,562,593 | 12/1985 | Ooe et al. | 382/134 |
| 4,700,298 | 10/1987 | Palcic et al. | 382/128 |
| 4,702,595 | 10/1987 | Mutschler et al. | 356/39 |
| 4,741,043 | 4/1988 | Bacus | 382/129 |

(List continued on next page.)

FOREIGN PATENT DOCUMENTS

| | | | |
|---|---|---|---|
| 0 595 506 A2 | 4/1994 | European Pat. Off. | G01N 21/00 |
| 0 595 506 A2 | 5/1994 | European Pat. Off. | G01N 21/00 |
| 0 610 916 A2 | 8/1994 | European Pat. Off. | G06F 15/68 |
| 4-322534 | 11/1992 | Japan | H04L 7/08 |
| WO90/10277 | 9/1990 | WIPO | G06K 9/34 |
| WO91/15826 | 10/1991 | WIPO | G06F 15/18 |
| WO93/16436 | 8/1993 | WIPO | G06F 15/00 |
| WO93/16442 | 8/1993 | WIPO | G06K 9/00 |
| WO96/09594 | 3/1996 | WIPO | G06F 159/00 |
| WO96/09605 | 3/1996 | WIPO | G06K 9/00 |

OTHER PUBLICATIONS

Bertrand, Dominique, et al., "Basic of Video Image Analysis," *Trends in Analytical Chemistry*, vol. 10, No. 8, Sep. 1991, pp. 237–243.

Bibbo, Marluce et al., "Chromatin Appearance in Intermediate Cells from Patients with Uterine Cancer," *Acta Cytologica*, vol. 25, No. 1, Jan.–Feb. 1981, pp. 23–28.

*BMDP Statistical Software Manual*, vol. 2, extract, University of California Press, 1988.

Bulstra, S.K., et al., "Thionin Staining of Paraffin and Plastic Embedded Sections of Cartilage," *Biotechnic & Histochemistry*, vol. 68, No. 1, 1993, pp. 20–28.

(List continued on next page.)

*Primary Examiner*—Jose L. Couso
*Assistant Examiner*—Anh Hong Do
*Attorney, Agent, or Firm*—Christensen O'Connor Johnson & Kindness pllc

[57] ABSTRACT

A system and method for detecting diagnostic cells and cells having malignancy-associated changes are disclosed. The system includes an automated classifier having a microscope, camera, image digitizer, a computer system for controlling and interfacing these components, a primary classifier for initial cell classification, and a secondary classifier for subsequent cell classification. The method utilizes the automated classifier to automatically detect diagnostic cells and cells having malignancy-associated changes. The system and method are particularly useful for detecting these cells in cell samples obtained from bronchial specimens such as lung sputum.

23 Claims, 14 Drawing Sheets

U.S. PATENT DOCUMENTS

| | | | |
|---|---|---|---|
| 4,907,158 | 3/1990 | Kettler et al. | 700/58 |
| 4,965,725 | 10/1990 | Rutenberg | 364/413.1 |
| 4,998,284 | 3/1991 | Bacus et al. | 382/133 |
| 5,016,283 | 5/1991 | Bacus et al. | 382/129 |
| 5,031,099 | 7/1991 | Kettler | 382/133 |
| 5,072,382 | 12/1991 | Kamentsky | 382/133 |
| 5,073,857 | 12/1991 | Peters et al. | 382/133 |
| 5,099,521 | 3/1992 | Kosaka | 382/133 |
| 5,109,429 | 4/1992 | Bacus et al. | 436/183 |
| 5,281,517 | 1/1994 | Bacus et al. | 435/6 |
| 5,287,272 | 2/1994 | Rutenberg et al. | 364/413.01 |
| 5,317,644 | 5/1994 | Kenyon et al. | 382/133 |
| 5,485,527 | 1/1996 | Bacus et al. | 382/128 |
| 5,544,650 | 8/1996 | Boon et al. | 128/632 |
| 5,627,908 | 5/1997 | Lee et al. | 382/133 |

OTHER PUBLICATIONS

Burger, G. et al., "Changes in benign cell population in cases of cervical cancer and its precursors," *Analytical and Quantitative Cytology,* vol. 3, 1981, pp. 261–271.

Cooper, J.D., et al., "Accurate Counting of Neurons in Frozen Sections: Some Necessary Precautions," *J. Anatomy,* vol. 157, 1988, pp. 13–21.

Danielsson, Per–Erik, "A New Shape Factor," *Computer Graphics and Image Processing,* vol. 7, 1978, pp. 292–299.

Doudkine, A., et al., "Nuclear Texture Measurements in Image Cytometry," *Pathologica,* vol. 87, 1995, pp. 286–299.

Eddy, D.M., "Screening for Lung Cancer," *Annals of Internal Medicine,* vol. 111, No. 3, Aug. 1, 1989, pp. 232–237.

Feulgen, R., et al., *Z. Physiol. Chem.* vol. 136, 1924, pp. 57–61.

Galloway, Mary M., "Texture Analysis Using Gray Level Run Lengths," *Computer Graphics and Image Processing,* vol. 4, 1975, pp. 172–179.

Garner, D.M., "The Cyto–Savant™ System," *The Automation of Cervical Cancer Screening,* H.K. Grohs et al., eds., Igakuk–Shoin Medical Publishers, Inc., New York, New York, 1994.

Garner, D.M., et al., "CytoSavant and Its Use in Automated Screening of Cervical Smears," in Compendium on the Computerized Cytology and Histology Laboratory, Wied, G.L., et al., eds., Tutorials of Cytology, Chicago, IL, 1994, pp. 346–352.

Holmquist, J. et al., "Computer Analysis of Cervical Cells Automatic Feature Extraction and Classification," *The Journal of Histochemistry and Cytochemistry,* vol. 26, No. 11, 1978, pp. 100–1017.

Humason, Gretchen L., Animal Tissue Techniques, 4th Ed., W.H. Freeman & Company, San Francisco, 1979, pp. 154–155, 181–183, 208, 316–319, 432–433, 471–473.

Insausti, R., et al., "The Human Entorhinal Cortex: A Cytoarchitectonic Analysis," *The Journal of Comparative Neurology,* vol. 355, 1995, pp. 171–198.

Jaggi, B., et al., "Design of a Solid–State Microscope," *Optical Engineering,* Jun. 1989, vol. 28 No. 6, pp. 675–682.

Jaggi, B., et al., "The Design and Development of an Optical Scanner for Cell Biology," *IEEE Proceedings Engineering in Medicine and Biology Society,* vol. 2, Sep. 1985; pp. 980–985.

Katzko, Michael W. et al., "Carcinoma In Situ Specimen Classification Based on Intermediate Cell Measurements," *Cytometry,* vol. 8, 1987, pp. 9–13.

Klawe, H. et al., "Malignancy associated changes (MAC) in cells of buccal smears detected by means of objective image analysis," *Acta Cytologica,* vol. 18, 1974, pp. 30–33.

Komitowski, D. et al., "Quantitative Description of Chromatin Structure During Neoplasia by the Method of Image Processing," *Analytical and Quantitative Cytology and Histology,* vol. 7, No. 3, Sep. 1985, pp. 178–182.

Kutscher, Charles L., et al., "Hematoxylin and Thionin Techniques for Staining Myelin and Cells: Variations and Critical Steps," *Brain Research Bulletin,* vol. 19, 1987, pp. 161–163.

Lockart, Royce Z., "Features Independent of Stain Intensity for Evaluating Feulgen–Stained Cells," *Analytical and Quantitative Cytology,* vol. 6, No. 2, Jun. 1984, pp. 105–111.

MacAulay, C. et al., "Fractal Texture Features Based on Optical Density Surface Area: Use in Image Analysis of Cervical Cells," *Analytical and Quantitative Cytology and Histology,* vol. 12, No. 6, Dec. 1990, pp. 394–398.

MacAulay, C. et al., "Malignancy–Associated Changes in Bronchial Epithelial Cells in Biopsy Specimens," *Analytical and Quantitative Cytology and Histology,* vol. 17, No. 1, Feb. 1995, pp. 55–61.

MacAulay, Calum and Branko Palcic, "An Edge Relocation Segmentation Algorithm," *Analytical and Quantitative Cytology and Histology,* vol. 12, No. 3, Jun. 1990, pp. 165–171.

Mickel, Ulrika V., et al., "A Comparative Study of Quantitative Stains for DNA in Image Cytometry," *Analytical and Quantitative Cytology and Histology,* vol. 13, No. 4, Aug. 1991, pp. 253–260.

Muto, Tetsuichiro, et al., "Mucin Abnormality in Colonic Mucosa in Patients with Familial Polyposis Coli," *Seminars in Surgical Oncology,* vol. 3, 1987, pp. 179–182.

Nieburgs, H.E. et al., "Systemic Cellular Changes in Material from Human and Animal Tissues," *Transactions,* 7th Annual Meeting Inter. Soc. Cytol. Council, 1959, pp. 137–144.

Ota, H., et al., "A Dual Staining Method for Identifying Mucins of Different Gastric Epithelial Mucous Cells," *Histochemical Journal,* vol. 23, 1991, pp. 22–28.

Palcic, B. et al., "Algorithms in Preparation for Decision–Making," *The Automation of Cervical Cancer Screening,* H.K. Grohs et al., eds., Igaku–Shoin Medical Publishers, Inc., N.Y., N.Y., 1994.

Palcic, B. et al., "Malignancy Associated Changes (MACs) and their Use in the Diagnosis and Prognosis of Early Cancer," presented at the Eighth International Meeting of the Adriatic Society of Pathology, Italy, Jun. 26–27, 1993.

Palcic, B. et al., "Malignancy Associated Changes: Can They be Employed Clinically?" *Compendium on the Computerized Cytology and Histology Laboratory,* George L. Wied et al., eds., Tutorials of Cytology, Chicago, Illinois, 1994, pp. 157–165.

Palcic, B. et al., "Quantitative Evaluation of Malignant Potential of Early Breast Cancer Using High Resolution Image Cytometry," presented at Chemoprevention of Breast Cancer: Surrogate Endpoints and Chemopreventive Agents in Short–term Clinical Trials, sponsored by the National Cancer Institute, Lake Tahoe, California, Oct. 5–10, 1993.

Payne, P.W. et al., "Diagnostic Variation on Bronchial Biopsy Specimens: Differential Diagnosis by Quantitative Features," presented at the XVI Congress of the International Society for Analytic Cytology, Colorado Springs, Colorado, Mar. 21–26, 1993; *Cytometry Supplement,* vol. 6, No. 84, Abstract #442, 1993.

Peet, F.G. et al., "A Computer–Assisted Cell Identification System," *Analytical and Quantitative Cytology,* vol. 6, No. 1, Mar. 1984, pp. 59–70.

Poon, S.S.S., et al., "Cell Recognition Algorithms for the Cell Analyzer," *IEEE Proceedings Engineering in Medicine and Biology Society,* vol. 4, Nov. 1987; pp. 1454–1456.

Pressman, Norman J., "Markovian Analysis of Cervical Cell Images," *The Journal of Histochemistry and Cytochemistry,* vol. 24, No. 1, 1976, pp. 138–144.

Russ, John C., *Computer–Assisted Microscopy, The Measurement and Analysis of Images,* Plenum Press, 1990, pp. 67–68.

Russ, John C., *The Image Processing Handbook* extract, CRC Press, 1992, pp. 225–228.

Schulte, E., et al., "The Influence of Cationic Thiazine Dyes on Eosin Y–Uptake of Red Blood Cells in Romanowsky–Giemsa Type," *Acta Histochemica,* Suppl.–Band XXXVII, S., 1989, pp. 139–147.

Schulte, Erik, M.D., "Air Drying as a Preparatory Factor in Cytology: Ivestigation of its Influence on Dye Uptake and Dye Binding," *Diagnostic Cytopathology,* vol. 2, No. 2, Apr.–Jun. 1986, pp. 160–167.

Schulte, Erik, M.D., et al., "Standardization of the Papanicolaou Stain: I. A Comparison of Five Nuclear Stains," *Analytical and Quantitative Cytology and Histology,* vol. No. 3, Jun. 1990, pp. 149–156.

Smeulders, Arnold W.M. et al., "Measurement Issues in Morphometry," *Analytical and Quantitative Cytology and Histology,* vol. 7, No. 4, Dec. 1985, pp. 242–249.

Tolivia, J., et al., "Differential Technique to Stain Nerve Cells and Fibers in Methacrylate Sections," *The Anatomical Record,* vol. 217, 1987, pp. 318–320.

Tolivia, J., et al., "Differential Thionin Block Staining of Nerve Cells and Fibers for Paraffin–Embedded Material in Mammalian Central Nervous System," *Neuroscience Letters,* vol. 102, 1989, pp. 155–158.

Toth, B.V.O., et al., "Malignancy Associated Changes in Sputum: A Correlated Study of 315 Patients," *Acta Cytologica,* vol. 19, No. 6, Nov.–Dec. 1975, pp. 573–576.

Unser, Michael, "Sum and Difference Histograms for Texture Classification," *IEEE Transactions on Pattern Analysis and Machine Intelligence,* vol. PAMI–8, No. 1, Jan. 1986, pp. 118–125.

Van Duijn, P., "A Histochemical Specific Thionine–$SO_2$ Reagent and its Use in a Bi–Color Method for Deoxyribonucleic Acid and Periodic Acid Schiff Positive Substances," *J. Histochem. Cytochem.,* vol. 4, 1956, pp. 55–63.

Ventrani, A., et al., "Malignancy–Associated Cellular Markers (MAC) in Oral and Bronchial Epithelial Cells in Sputum Specimens: Possible Morphologic Marker for High–Risk Groups (Asbestos–Exposed Workers)," *Cancer Detection and Prevention,* vol. 9, 1986, pp. 343–346.

Winzek, C., et al., "An Improved Method to Investigate Staining Kinetics in Single Cells," *Histochemistry,* vol. 86, 1987, pp. 421–426.

Winzek, C., et al., "Staining Kinetics in Single Cells: Part II. Diffusion Processes Inside the Cell," *Histochemistry,* vol. 90, 1988, pp. 79–83.

6,026,174

SYSTEM AND METHOD FOR AUTOMATICALLY DETECTING MALIGNANT CELLS AND CELLS HAVING MALIGNANCY-ASSOCIATED CHANGES

RELATED APPLICATIONS

The present application is a continuation-in-part of applications Ser. No. 08/888,434 filed Jul. 7, 1997, entitled COMPOSITION AND METHOD FOR STAINING CELLULAR DNA, Attorney Docket No. ONIC110769, now U.S. Pat. No. 5,942,410, and Ser. No. 08/644,893 filed May 10, 1996, U.S. Pat. No. 5,889,881, which was a continuation-in-part of Ser. No. 08/425,257 filed Apr. 17, 1995, now abandoned, which was a continuation of Ser. No. 08/182,453 filed Jan. 10, 1994, now abandoned, which was a continuation-in-part of Ser. No. 07/961,596 filed Oct. 14, 1992, now abandoned, the disclosures of which are incorporated by reference. The benefit of the filing dates of the previous applications are claimed under 35 U.S.C. § 120.

FIELD OF THE INVENTION

The present invention relates to image cytometry systems and cell classification in general, and in particular to automated systems for detecting malignant cells and cells having malignancy-associated changes.

BACKGROUND OF THE INVENTION

The most common method of diagnosing cancer in patients is by obtaining a sample of the suspect tissue and examining it under a microscope for the presence of obviously malignant cells. While this process is relatively easy when the location of the suspect tissue is known, it is not so easy when there is no readily identifiable tumor or pre-cancerous lesion. For example, to detect the presence of lung cancer from a sputum sample requires one or more relatively rare cancer cells to be present in the sample. Therefore patients having lung cancer may not be diagnosed properly if the sample does not accurately reflect the conditions of the lung.

Malignancy-associated changes (MACs) are subtle changes that are known to take place in the nuclei of apparently normal cells found near cancer tissue. In addition, MACs have been detected in tissue found near pre-cancerous lesions. Because the cells exhibiting MACs are more numerous than the malignant cells, MACs offer an additional way of diagnosing the presence of cancer, especially in cases where no cancerous cells can be located.

Despite the ability of researchers to detect MACs in patients known to have cancer or a pre-cancerous condition, MACs have not yet achieved wide acceptance as a screening tool to determine whether a patient has or will develop cancer. Traditionally, MACs have been detected by carefully selecting a cell sample from a location near a tumor or pre-cancerous lesion and viewing the cells under relatively high magnification. However, it is believed that the malignancy-associated changes that take place in the cells are too subtle to be reliably detected by a human pathologist working with conventional microscopic equipment, especially when the pathologist does not know beforehand if the patient has cancer or not. For example, a malignancy-associated change may be indicated by the distribution of DNA within the nucleus coupled with slight variations in the shape of the nucleus edge. However, nuclei from normal cells may exhibit similar types of changes but not to the degree that would signify a MAC. Because human operators cannot easily quantify such subtle cell changes, it is difficult to determine which cells exhibit MACs. Furthermore, the changes which indicate a MAC may vary between different types of cancer, thereby increasing the difficulty of detecting them.

SUMMARY OF THE INVENTION

The present invention is a system for automatically detecting malignancy-associated changes in cell samples. The system includes a digital microscope having a CCD camera that is controlled by and interfaced with a computer system. Images captured by the digital microscope are stored in an image processing board and manipulated by the computer system to detect the presence of malignancy-associated changes (MACs). At the present state of the art, it is believed that any detection of MACs requires images to be captured at a high spatial resolution, a high photometric resolution, that all information coming from the nucleus is in focus, that all information belongs to the nucleus (rather than some background), and that there is an accurate and reproducible segmentation of the nucleus and nuclear material. Each of these steps is described in detail below.

To detect the malignancy-associated changes, a cell sample is obtained and stained to identify the nuclear material of the cells and is imaged by the microscope. The stain is stoichiometric and specific to DNA only. The computer system then analyzes the image to compute a histogram of all pixels comprising the image. First, an intensity threshold is set that divides the background pixels from those comprising the objects in the image. All pixels having an intensity value less than the threshold are identified as possible objects of interest while those having an intensity value greater than the threshold are identified as background and are ignored.

For each object located, the computer system calculates the area, shape and optical density of the object. Those objects that could not possibly be cell nuclei are ignored. Next, the image is decalibrated, i.e., corrected by subtracting an empty frame captured before the scanning of the slide from the current frame and adding back an offset value equal to the average background light level. This process corrects for any shading of the system, uneven illumination, and other imperfections of the image acquisition system. Following decalibration, the images of all remaining objects must be captured in a more precise focus. This is achieved by moving the microscope in the stage z-direction in multiple focal planes around the approximate frame focus. For each surviving object a contrast function (a texture feature) is calculated. The contrast function has a peak value at the exact focus of the object. Only the image at the highest contrast value is retained in the computer memory and any object which did not reach such a peak value is also discarded from further considerations.

Each remaining in-focus object on the image is further compensated for local absorbency of the materials surrounding the object. This is a local decalibration which is similar to that described for the frame decalibration described above, except that only a small subset of pixels having an area equal to the area of a square into which the object will fit is corrected using an equivalent square of the empty frame.

After all images are corrected with the local decalibration procedure, the edge of the object is calculated, i.e., the boundary which determines which pixels in the square belong to the object and which belong to the background. The edge determination is achieved by the edge-relocation algorithm. In this process, the edge of the original mask of the first contoured frame of each surviving object is dilated for several pixels inward and outward. For every pixel in this frame a gradient value is calculated, i.e., the sum and difference between all neighbor pixels touching the pixel in question. Then the lowest gradient value pixel is removed from the rim, subject to the condition that the rim is not ruptured. The process continues until such time as a single pixel rim remains. To ensure that the proper edge of an object is located, this edge may be again dilated as before, and the process repeated until such time as the new edge is identical to the previous edge. In this way the edge is calculated along the highest local gradient.

The computer system then calculates a set of feature values for each object. For some feature calculations the edge along the highest gradient value is corrected by either dilating the edge by one or more pixels or eroding the edge by one or more pixels. This is done such that each feature achieves a greater discriminating power between classes of objects and is thus object specific. These feature values are then analyzed by a classifier that uses the feature values to determine whether the object is an artifact or is a cell nucleus. If the object appears to be a cell nucleus, then the feature values are further analyzed by the classifier to determine whether the nucleus exhibits malignancy-associated changes. Based on the number of objects found in the sample that appear to have malignancy-associated changes and/or an overall malignancy-associated score, a determination can be made whether the patient from whom the cell sample was obtained is healthy or harbors a malignant growth.

In another aspect, the present invention provides a system and method for automatically detecting diagnostic cells and cells having malignancy-associated changes. The system is an automated classifier and includes, in addition to a microscope, camera, image digitizer, and computer system for controlling and interfacing these components, a primary classifier for preliminarily classifying a cytological specimen and a secondary classifier for classifying those portions of the cytological sample initially classified by the primary classifier. The primary classifier distinguishes and selects epithelial cells from among abnormal cells, such as diagnostic cells, in the cell sample based on one set of features. The secondary classifier indicates whether the selected epithelial cells are normal or have malignancy-associated changes based on a second set of features. The system and method are particularly useful for detecting diagnostic cells and cells having malignancy-associated changes in cell samples obtained from a variety of sources including cells obtained from bronchial specimens such as lung sputum.

In other embodiments, the present invention provides a method for detecting epithelial cells in a cell sample and a method for detecting cells having malignancy-associated changes from among epithelial cells. In another embodiment, a method for predicting whether a patient will develop cancer is provided.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As described above, the present invention is a system for automatically detecting malignancy-associated changes (MACs) in the nuclei of cells obtained from a patient. From the presence or absence of MACs, a determination can be made whether the patient has a malignant cancer.

Figure 1:
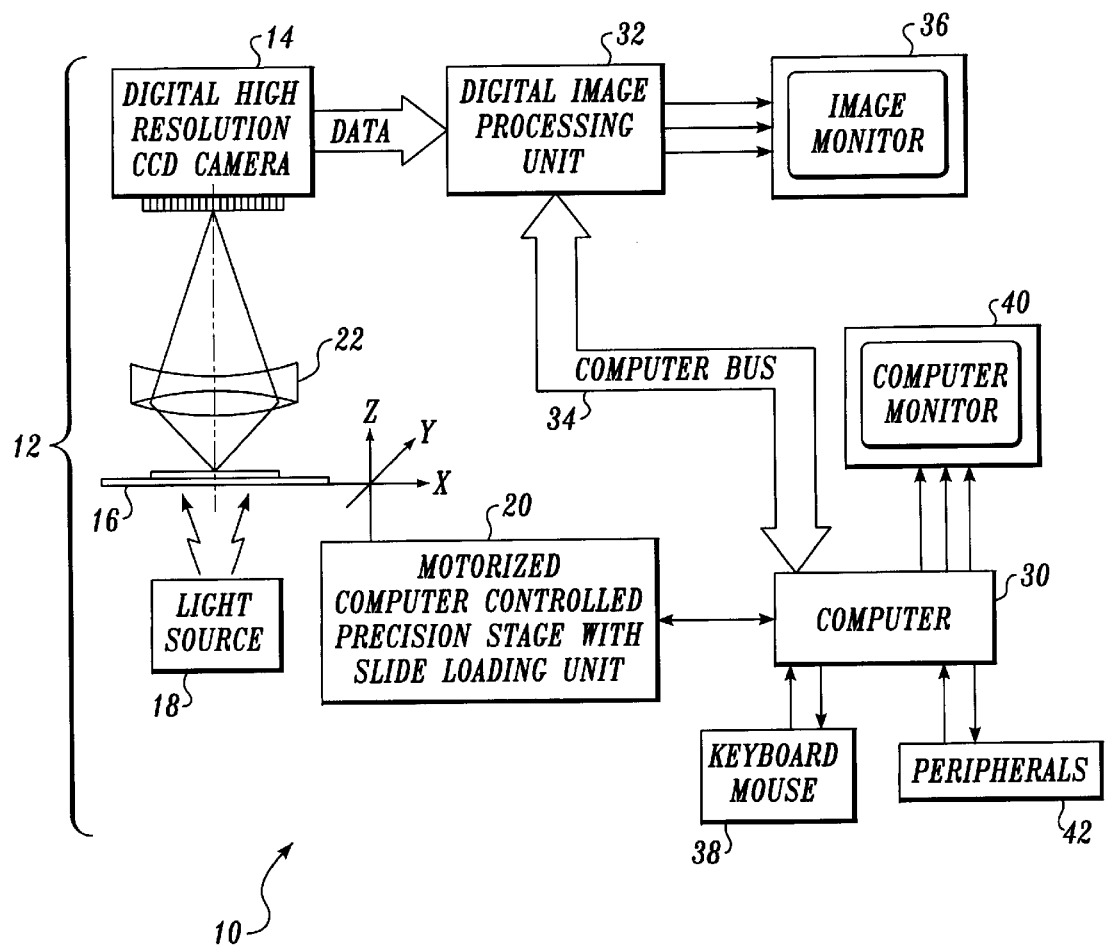
FIG. 1 is a block diagram of the MAC detection system according to the present invention.

A block diagram of the MAC detection system according to the present invention is shown in FIG. 1. The system 10 includes a digital microscope 12 that is controlled by and interfaced with a computer system 30. The microscope 12 preferably has a digital CCD camera 14 employing a scientific CCD having square pixels of approximately 0.3 $\mu$m by 0.3 $\mu$m size. The scientific CCD has a 100% fill factor and at least a 256 gray level resolution. The CCD camera is preferably mounted in the primary image plane of a planar objective lens 22 of the microscope 12.

A cell sample is placed on a motorized stage 20 of the microscope whose position is controlled by the computer system 30. The motorized stage preferably has an automatic slide loader so that the process of analyzing slides can be completely automated.

A stable light source 18, preferably with feedback control, illuminates the cell sample while an image of the slide is being captured by the CCD camera. The lens 22 placed between the sample 16 and the CCD camera 14 is preferably a 2x/0.75 objective that provides a depth of field in the range of 1–2 $\mu$m that yields a distortion-free image. In the present embodiment of the invention, the digital CCD camera 14 used is the Microimager™ produced by Xillix Technologies Corp. of Richmond, B.C., Canada.

The images produced by the CCD camera are received by an image processing board 32 that serves as the interface between the digital camera 14 and the computer system 30. The digital images are stored in the image processing board and manipulated to facilitate the detection of MACs. The image processing board creates a set of analog video signals from the digital image and feeds the video signals to an image monitor 36 in order to display an image of the objects viewed by the microscope.

The computer system 30 also includes one or more input devices 38, such as a keyboard and mouse, as well as one or more peripherals 42, such as a mass digital storage device, a modem or a network card for communicating with a remotely located computer, and a monitor 40.

Figure 2A:
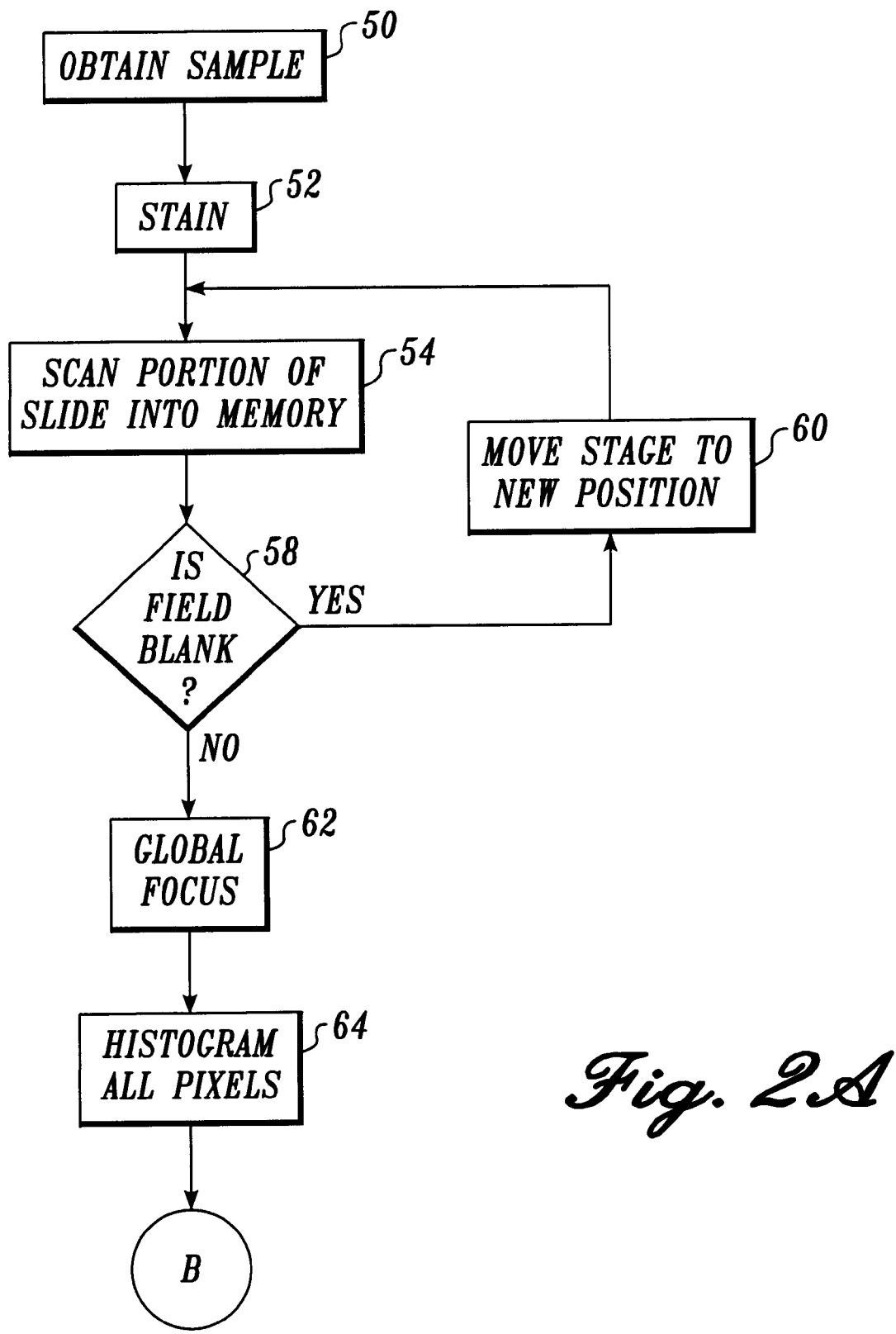
FIGS. 2A–2C are a series of flow charts showing the steps performed by the present invention to detect MACs.
Figure 2B:
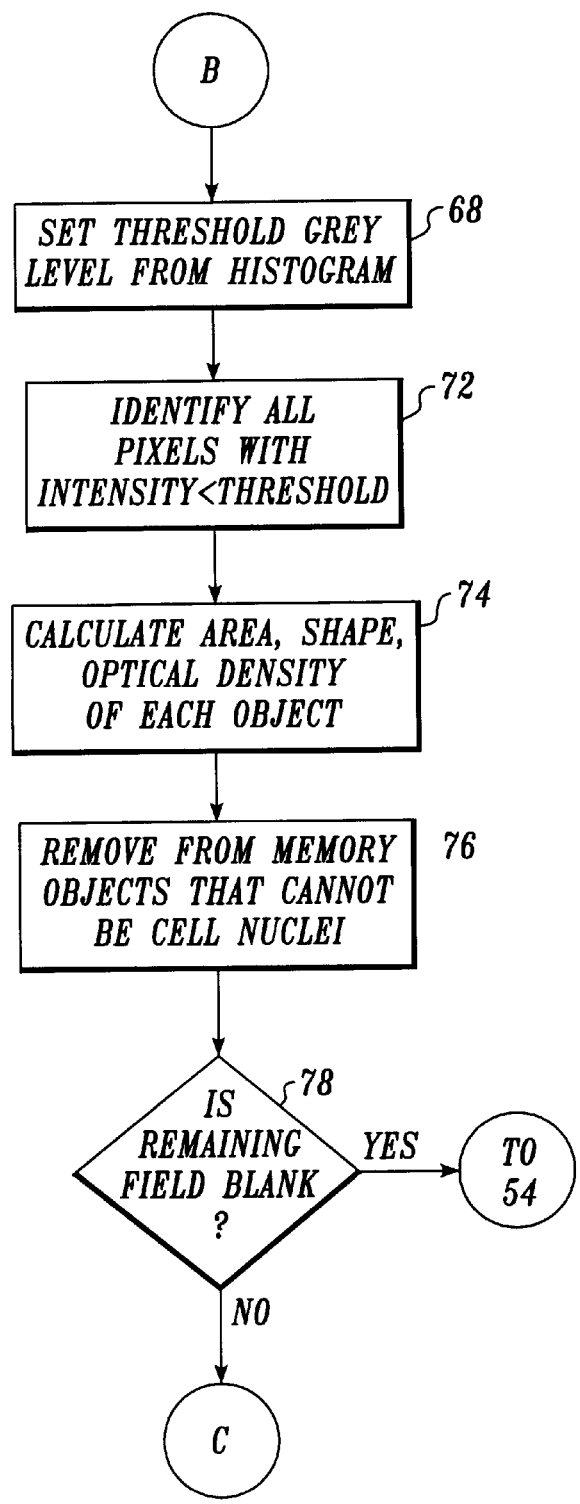
Figure 2C:
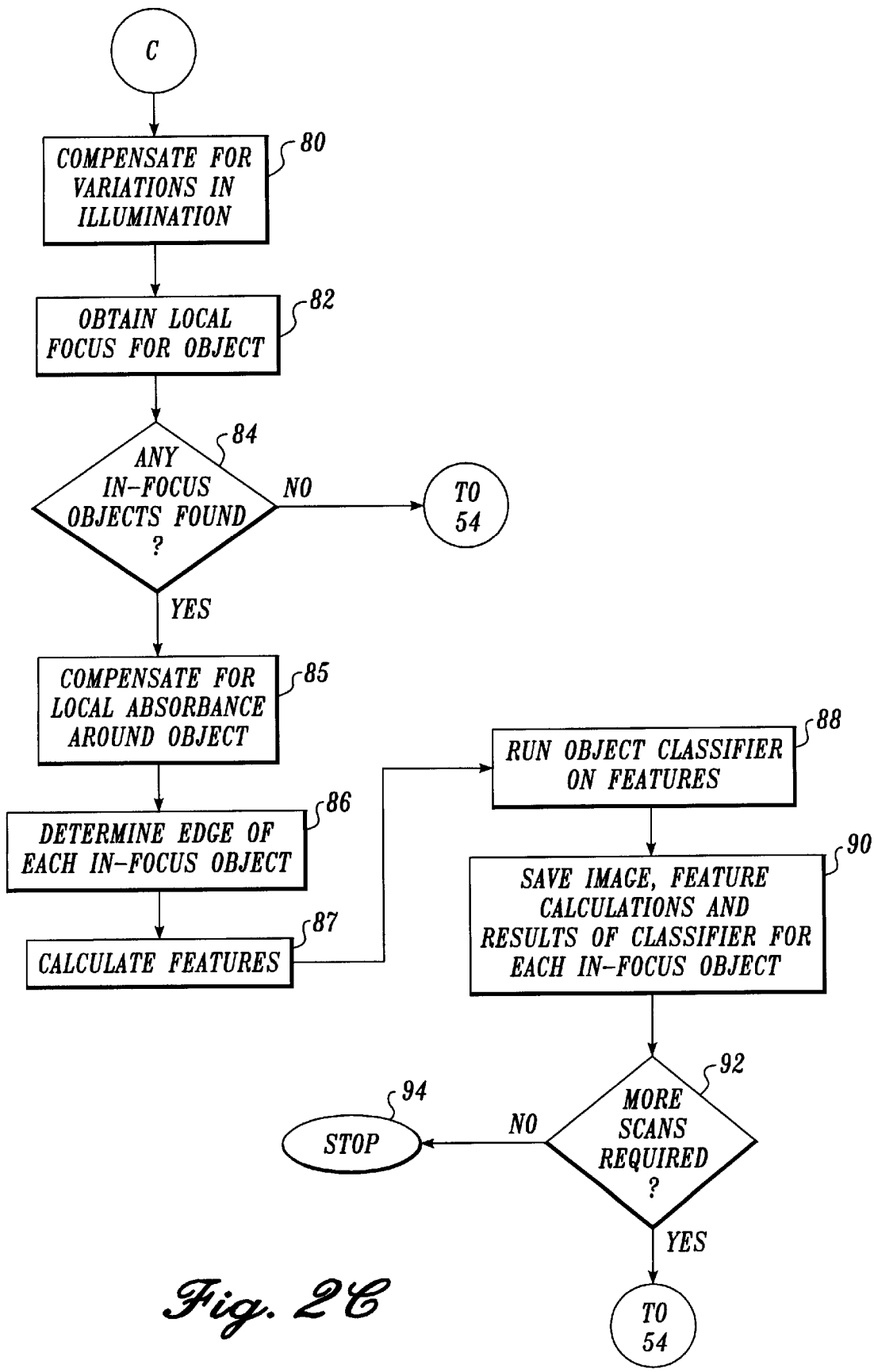
Figure 4:
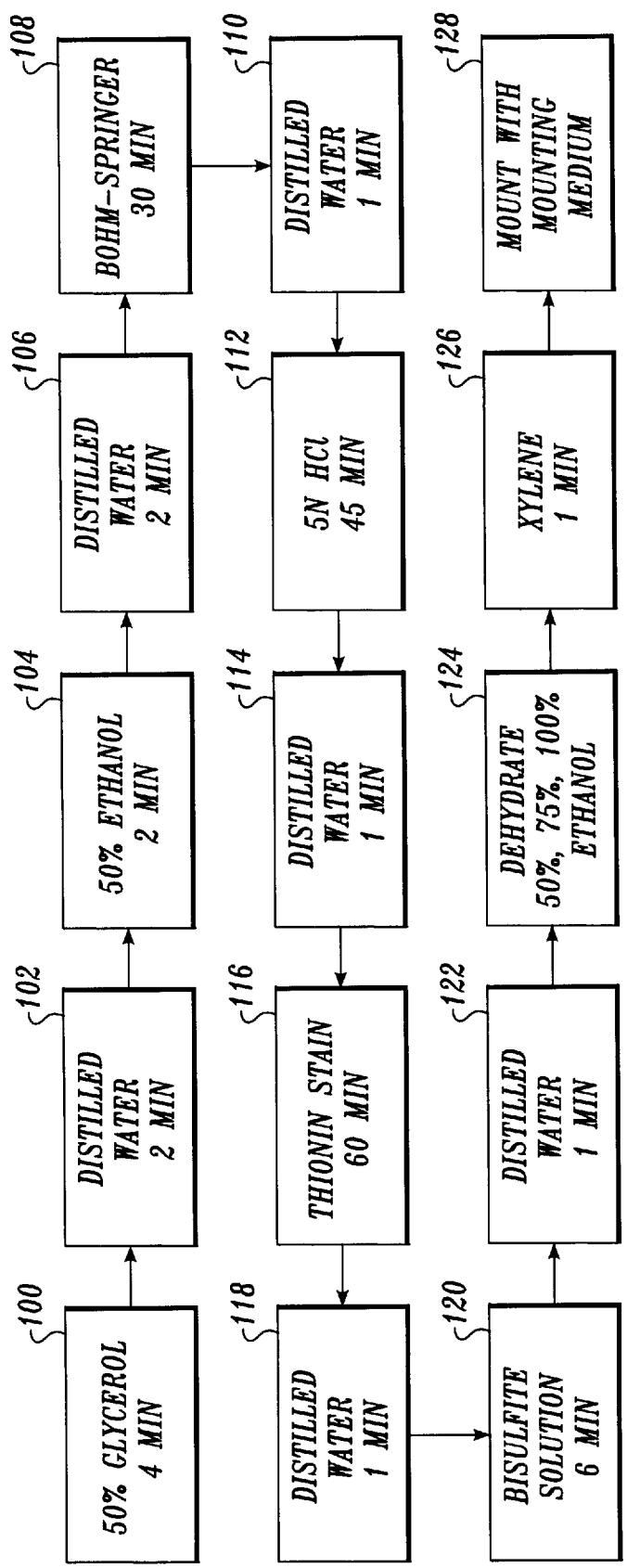
FIG. 4 is a flow chart of the preferred staining procedure used to prepare a cell sample for the detection of MACs.

FIGS. 2A–2C show the steps performed by the system of the present invention to determine whether a sample exhibits MACs or not. Beginning with a step 50, a cell sample is obtained. Cells may be obtained by any number of conventional methods such as biopsy, scraping, etc. The cells are affixed to a slide and stained using a modified Feulgen procedure at a step 52 that identifies the nuclear DNA in the sample. The details of the staining procedure are shown in FIG. 4 and described in detail below.

At step 54, an image of a frame from the slide is captured by the CCD camera and is transferred into the image processor. In this process, the CCD sensor within the camera is cleared and a shutter of the camera is opened for a fixed period that is dependent on the intensity of the light source 18. After the image is optimized according to the steps described below, the stage then moves to a new position on the slide such that another image of the new frame can be captured by the camera and transferred into the computer memory. Because the cell sample on the slide occupies a much greater area than the area viewed by the microscope, a number of slide images are used to determine whether the sample is MAC-positive or negative. The position of each captured image on the slide is recorded in the computer system so that the objects of interest in the image can be found on the slide if desired.

Once an image from the slide is captured by the CCD camera and stored in the image processing board, the computer system determines whether the image produced by the CCD camera is devoid of objects. This is performed by scanning the digital image for dark pixels. If the number of dark pixels, i.e., those pixels having an intensity of the background intensity minus a predetermined offset value, is fewer than a predetermined minimum, the computer system assumes that the image is blank and the microscope stage is moved to a new position at step 60 and a new image is captured at step 54.

If the image is not blank, then the computer system attempts to globally focus the image. In general, when the image is in focus, the objects of interest in the image have a maximum darkness. Therefore, for focus determination the height of the stage is adjusted and a new image is captured. The darkness of the object pixels is determined and the process repeats until the average darkness of the pixels in the image is a maximum. At this point, the computer system assumes that global focus has been obtained.

Figure 3:
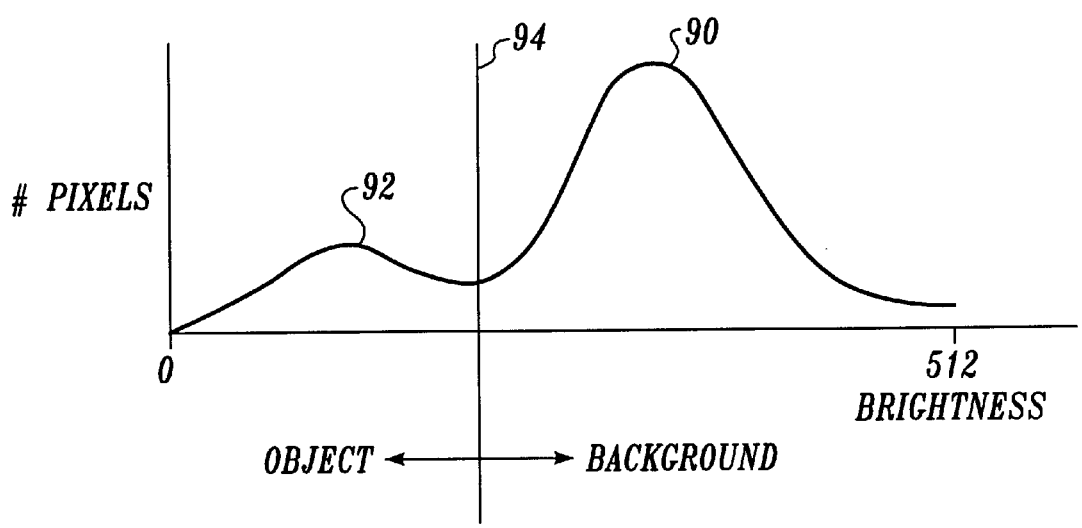
FIG. 3 is an illustrative example of a histogram used to separate objects of interest from the background of a slide.

After performing the rough, global focus at step 62, the computer system computes a histogram of all pixels. As shown in FIG. 3, a histogram is a plot of the number of pixels at each intensity level. In the Microimager™-based microscope system, each pixel can have an intensity ranging from 0 (maximum darkness) to 255 (maximum brightness). The histogram typically contains a first peak 90 that represents the average intensity of the background pixels. A second, smaller peak 92 represents the average intensity of the pixels that comprise the objects. By calculating a threshold 94 that lies between the peaks 90 and 92, it is possible to crudely separate the objects of interest in the image from the background.

Figure 5:
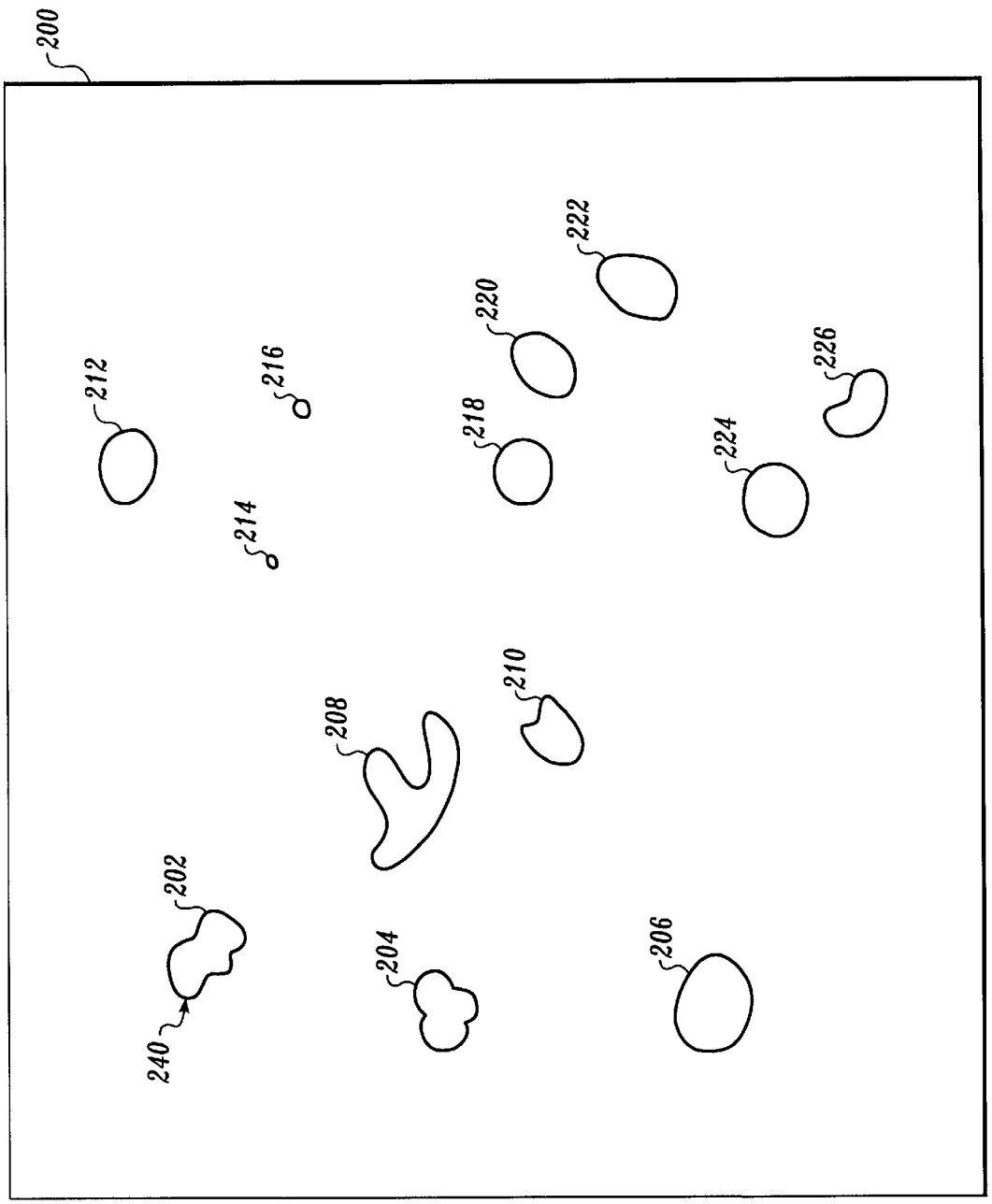
FIGS. 5 and 6 are illustrations of objects located in an image.

Returning to FIG. 2B, the computer system computes the threshold that separates objects in the image from the background at step 68. At a step 72, all pixels in the cell image having an intensity less than the threshold value are identified. The results of step 72 are shown in FIG. 5. The frame image 200 contains numerous objects of interest 202, 204, 206 . . . 226. Some of these objects are cell nuclei, which will be analyzed for the presence of MACs, while other objects are artifacts such as debris, dirt particles, white blood cells, etc., and should be removed from the cell image.

Returning to FIG. 2B, once the objects in the image have been identified, the computer system calculates the area, shape (sphericity) and optical density of each object according to formulas that are described in further detail below. At a step 76, the computer system removes from memory any objects that cannot be cell nuclei. In the present embodiment of the invention those objects that are not possibly cell nuclei are identified as having an area greater than 2,000 $\mu m^2$, an optical density less than 1 c (i.e., less that ½ of the overall chromosome count of a normal individual) or a shape or sphericity greater than 4.

Figure 6:
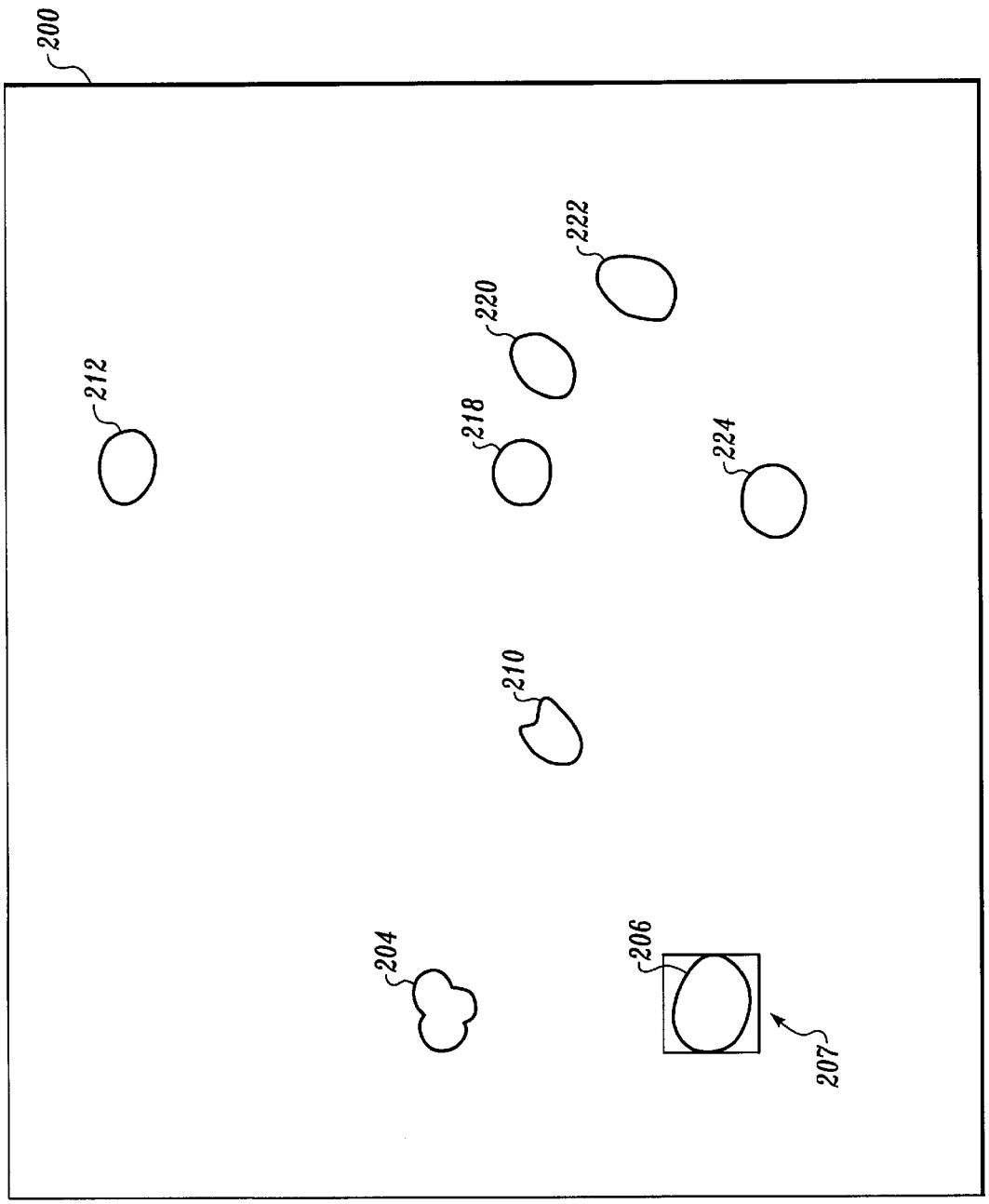

The results of step 76 are shown in FIG. 6 where only a few of the previously identified objects of interest remain. Each of the remaining objects is more likely to be a cell nuclei that is to be examined for a malignancy-associated change.

Again returning to FIG. 2B, after removing each of the objects that could not be a cell nucleus, the computer system determines whether there are any objects remaining by scanning for dark pixels at step 78. If no objects remain, the computer system returns to step 54, a new image on the slide is captured and steps 54–76 are repeated.

If there are objects remaining in the image after the first attempt at removing artifacts at step 76, the computer system then compensates the image for variations in illumination intensity at step 80. To do this, the computer system recalls a calibration image that was obtained by scanning in a blank slide for the same exposure time that was used for the image of the cells under consideration. The computer system then begins a pixel-by-pixel subtraction of the intensity values of the pixels in the calibration image obtained from the blank slide from the corresponding pixels found in the image obtained from the cell sample. The computer system then adds a value equal to the average illumination of the pixels in the calibration image obtained from the blank slide to each pixel of the cell image. The result of the addition illuminates the cell image with a uniform intensity.

Once the variations in illumination intensity have been corrected, the computer system attempts to refine the focus of each object of interest in the image at step 82 (FIG. 2C). The optimum focus is obtained when the object has a minimum size and maximum darkness. The computer system therefore causes the stage to move a predefined amount above the global focus position and then moves in a sequence of descending positions. At each position the CCD camera captures an image of the frame and calculates the area and the intensity of the pixels comprising the remaining objects. Only one image of each object is eventually stored in the computer memory coming from the position in which the pixels comprising the object have the maximum darkness and occupy a minimum area. If the optimum focus is not obtained after a predetermined number of stage positions, then the object is removed from the computer memory and is ignored. Once the optimum focus of the object is determined, the image received from the CCD camera overwrites those pixels that comprise the object under consideration in the computer's memory. The result of the local focusing produces a pseudo-focused image in the computer's memory whereby each object of interest is ultimately recorded at its best possible focus.

At a step 84, the computer system determines whether any in-focus objects in the cell image were found. If not, the computer system returns to step 54 shown in FIG. 2A whereby the slide is moved to another position and a new image is captured.

Once an image of the object has been focused, the computer system then compensates for local absorbency of light near the object at a step 85. To do this, the computer system analyzes a number of pixels within a box having an area that is larger than the object by two pixels on all sides. An example of such a box is the box 207 shown in FIG. 6. The computer system then performs a pixel-by-pixel subtraction of the intensity values from a corresponding square in the calibration image obtained from the blank slide. Next the average illumination intensity of the calibration image is added to each pixel in the box surrounding the object. Then the average intensity value for those pixels that are in the box but are not part of the object is determined and this local average value is then subtracted from each pixel in the box that encloses the object.

Once the compensation for absorbency around the object has been made, the computer system then determines a more precise edge of each remaining object in the cell image at step 86. The steps required to compute the edge are discussed in further detail below.

Having compensated for local absorbency and located the precise edge of the object, the computer system calculates a set of features for each remaining object at a step 87. These feature values are used to further separate artifacts from cell nuclei as well as to identify nuclei exhibiting MACs. The details of the feature calculation are described below.

At a step 88, the computer system runs a classifier that compares the feature values calculated for each object and determines whether the object is an artifact and, if not, whether the object is a nucleus that exhibits MACs.

At a step 90, the pseudo-focus digital image, the feature calculations and the results of the classifier for each in-focus object are stored in the computer's memory.

Finally, at a step 92, the computer system determines whether further scans of the slide are required. As indicated above, because the size of each cell image is much less than the size of the entire slide, a number of cell images are captured to ensure that the slide has been adequately analyzed. Once a sufficient number of cell images have been analyzed, processing stops at step 94. Alternatively, if further scans are required, the computer system loops back to step 54 and a new image of the cell sample is captured.

As indicated above, before the sample can be imaged by the digital microscope, the sample is stained to identify the nuclear material.

FIG. 4 is a flow chart of the steps used to stain the cell samples. Beginning at a step 100, the cell sample is placed on a slide, air dried and then soaked in a 50% glycerol solution for four minutes. The cell is then washed in distilled water for two minutes at a step 102. At a step 104, the sample is bathed in a 50% ethanol solution for two minutes and again washed with distilled water for two minutes at a step 106. The sample is then soaked in a Bohm-Springer solution for 30 minutes at a step 108 followed by washing with distilled water for one minute at a step 110. At step 112, the sample is soaked in a 5N HCl solution for 45 minutes and rinsed with distilled water for one minute at a step 114. The sample is then stained in a thionine stain for 60 minutes at a step 116 and rinsed with distilled water for one minute at a step 118.

At step 120, the sample is soaked in a bisulfite solution for six minutes followed by a rinse for one minute with distilled water at a step 122. Next, the sample is dehydrated in solutions of 50%, 75% and 100% ethanol for approximately 10 seconds each at a step 124. The sample is then soaked in a final bath of xylene for one minute at a step 126 before a cover slip is applied at a step 128. After the cell sample has been prepared, it is ready to be imaged by the digital microscope and analyzed as described above.

Figure 7A:
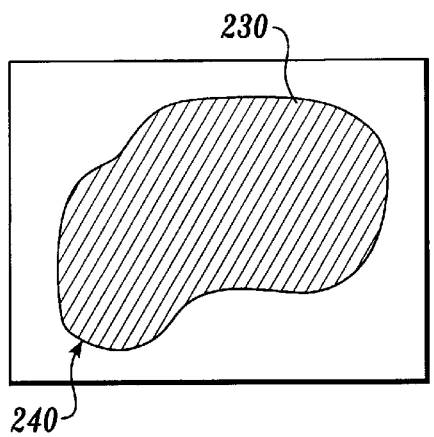
FIGS. 7A–7F illustrate how the present invention operates to locate the edge of an object.
Figure 7B:
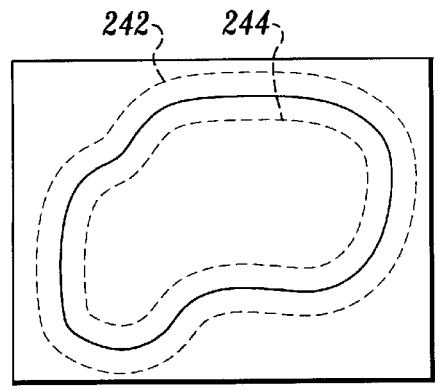

FIGS. 7A–7F illustrate the manner in which the present invention calculates the precise edge of an object. As shown in FIG. 7A, an object 230 is comprised of those pixels having an intensity value less than the background/object threshold which is calculated from the histogram and described above. In order to calculate the precise edge, the pixels lying at the original edge of the object are dilated to form a new edge region 242. A second band of pixels lying inside the original edge are also selected to form a second edge region 244. The computer system then assumes that the true edge is somewhere within the annular ring bounded by the edge regions 242 and 244. In the presently preferred embodiment of the invention, the annular ring has a width of approximately ten pixels. To determine the edge, the computer calculates a gradient for each pixel contained in the annular ring. The gradient for each pixel is defined as the sum of the differences in intensity between each pixel and its surrounding eight neighbors. Those pixels having neighbors with similar intensity levels will have a low gradient while those pixels at the edge of the object will have a high gradient.

Figure 7C:
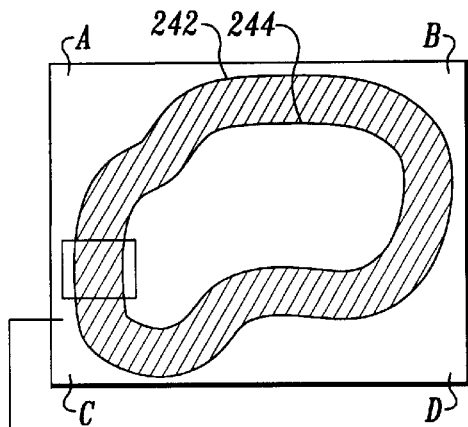

Once the gradients have been calculated for each pixel in the annular ring, the computer system divides the range of gradients into multiple thresholds and begins removing pixels having lower gradient values from the ring. To remove the pixels, the computer scans the object under consideration in a raster fashion. As shown in FIG. 7C, the raster scan begins at a point A and continues to the right until reaching a point B. During the first scan, only pixels on the outside edge, i.e., pixels on the edge region 242, are removed. The computer system then scans in the opposite direction by starting, for example, at point D and continuing upwards to point B returning in a raster fashion while only removing pixels on the inside edge region 244 of the annular ring. The computer system then scans in another orthogonal direction—for example, starting at point C and continuing in the direction of point D in a raster fashion, this time only removing pixels on the outside edge region 242. This process continues until no more pixels at that gradient threshold value can be removed.

Figure 7E:
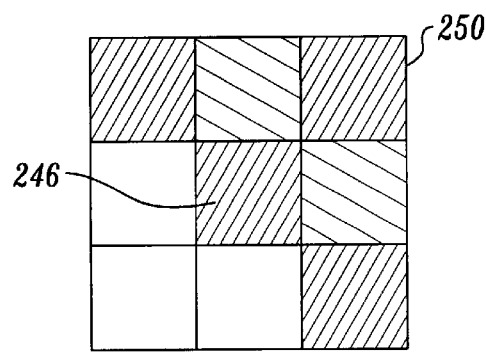
Figure 7D:
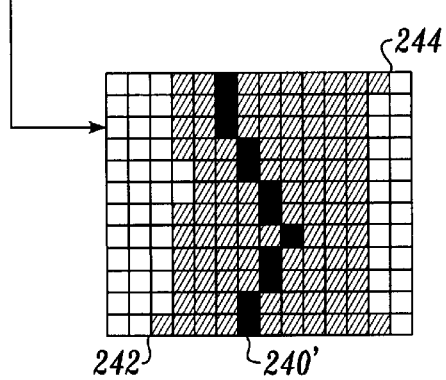

Pixels are removed from the annular ring subject to the conditions that no pixel can be removed that would break the chain of pixels around the annular ring. Furthermore, adjacent pixels cannot be removed during the same pass of pixel removal. Once all the pixels are removed having a gradient that is less than or equal to the first gradient threshold, the threshold is increased and the process starts over. As shown in FIG. 7D, the pixel-by-pixel removal process continues until a single chain of pixels 240' encircles the object in question.

Figure 7F:
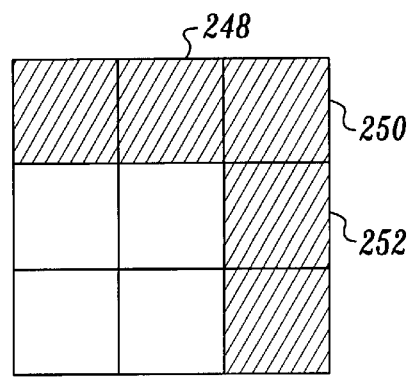

After locating the precise edge of an object, it is necessary to determine whether those pixels that comprise the edge should be included in the object. To do this, the intensity of each pixel that comprises the newly found edge is compared with its eight neighbors. As shown in FIG. 7E, for example, the intensity of a pixel 246 is compared with its eight surrounding pixels. If the intensity of pixel 246 is less than the intensity of pixel 250, then the pixel 246 is removed from the pixel chain as it belongs to the background. To complete the chain, pixels 248 and 252 are added so that the edge is not broken as shown in FIG. 7F. After completing the edge relocation algorithm and determining whether each pixel should be included in the object of interest, the system is ready to compute the feature values for the object.

Once the features have been calculated for each in-focus object, the computer system must make a determination whether the object is a cell nucleus that should be analyzed for malignancy-associated changes or is an artifact that should be ignored. As discussed above, the system removes obvious artifacts based on their area, shape (sphericity) and optical density. However, other artifacts may be more difficult for the computer to recognize. To further remove artifacts, the computer system uses a classifier that interprets the values of the features calculated for the object.

Figure 8:
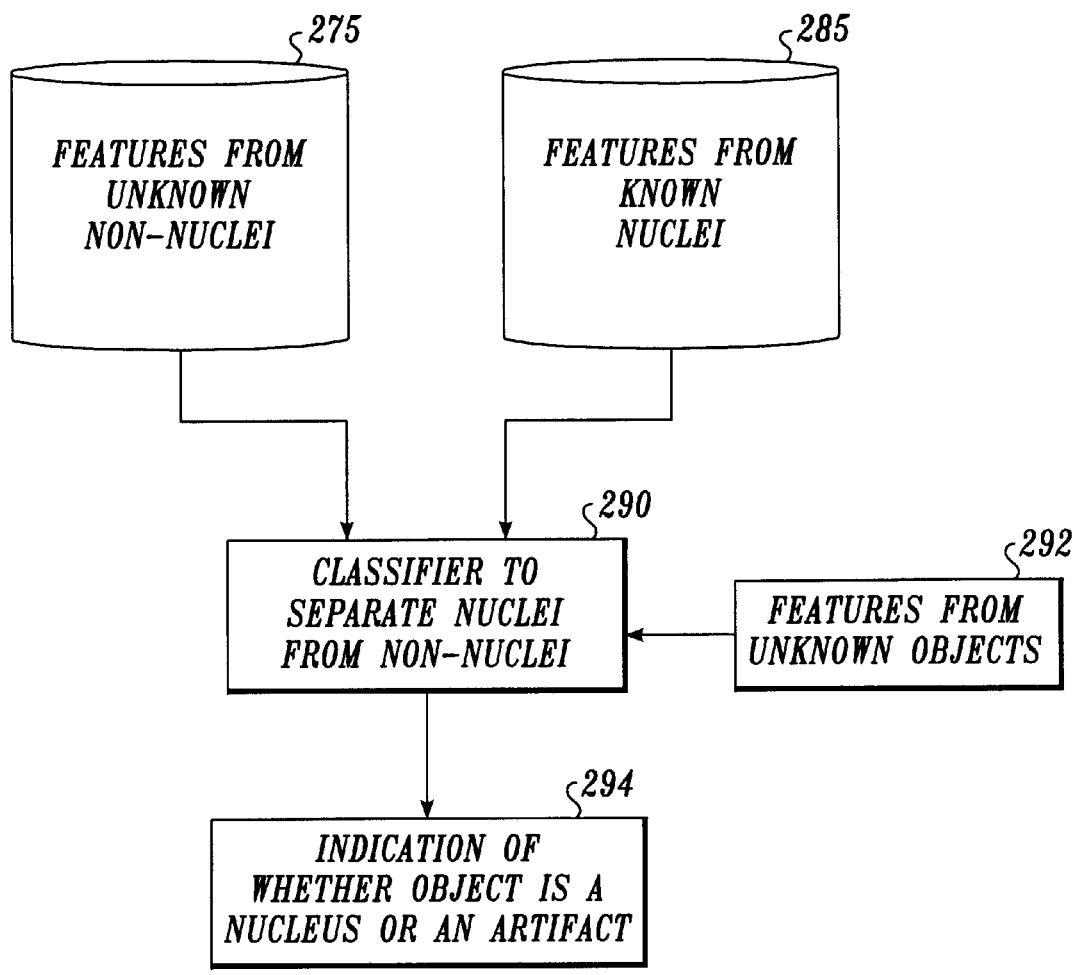
FIGS. 8 and 9 are diagrammatic illustrations of a classifier that separates artifacts from cell nuclei and MAC nuclei from non-MAC nuclei.

As shown in FIG. 8, a classifier 290 is a computer program that analyzes an object based on its feature values. To construct the classifier two databases are used. The first database 275 contains feature values of objects that have been imaged by the system shown in FIG. 1 and that have been previously identified by an expert pathologist as non-nuclei, i.e., artifacts. A second database 285 contains the features calculated for objects that have been imaged by the system and that have been previously identified by an expert as cell nuclei. The data in each of these databases is fed into a statistical computer program which uses a stepwise linear discriminant function analysis to derive a discriminant function that can distinguish cell nuclei from artifacts. The classifier is then constructed as a binary decision tree based on thresholds and/or the linear discriminant functions. The binary tree answers a series of questions based on the feature values to determine the identity of an object.

The particular thresholds used in the binary tree are set by statisticians who compare histograms of feature values calculated on known objects. For example, white blood cells typically have an area less than 50 $\mu m^2$. Because the present invention treats a white blood cell as an artifact, the binary decision tree can contain a node that compares the area of an object to the 50 $\mu m^2$ threshold. Objects with an area less than the threshold are ignored while those with an area having a greater area are further analyzed to determine if they are possible MAC cells or artifacts.

In the presently preferred embodiment of the invention, the discriminant functions that separate types of objects are generated by the BMDP program available from BMDP Statistical Software, Inc., of Los Angeles, Calif. Given the discriminant functions and the appropriate thresholds, the construction of the binary tree classifier is considered routine for one of ordinary skill in the art.

Once the binary tree classifier has been developed, it can be supplied with a set of feature values 292 taken from an unknown object and will provide an indication 294 of whether the object associated with the feature data is most likely an artifact or a cell nucleus.

Figure 9:
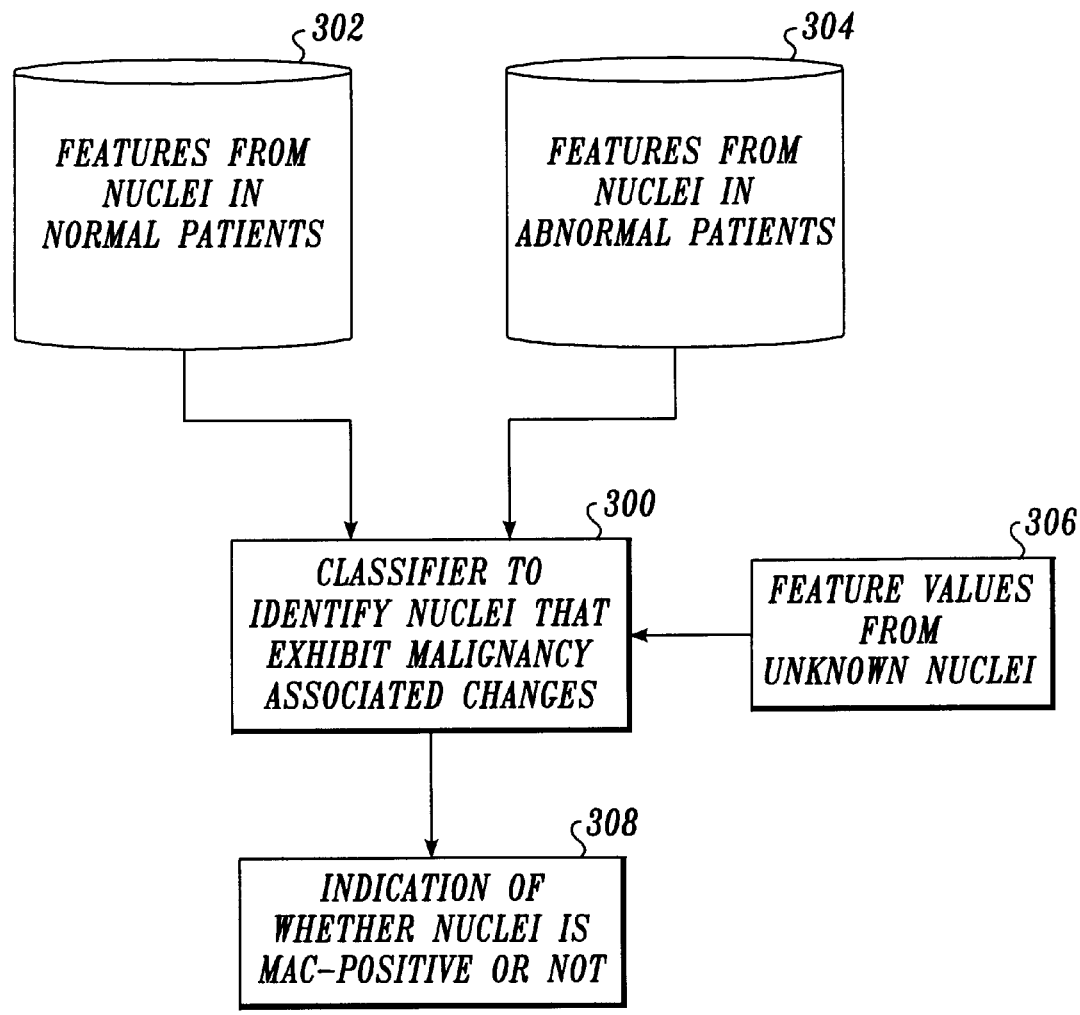

FIG. 9 shows how a classifier is used to determine whether a slide exhibits malignancy-associated changes or not. The classifier 300 is constructed using a pair of databases. A first database 302 contains feature values obtained from apparently normal cells that have been imaged by the digital microscope system shown in FIG. 1 and are known to have come from healthy patients. A second database 304 contains feature values calculated from apparently normal cells that were imaged by the digital microscope system described above and were known to have come from abnormal (i.e., cancer) patients. Again, classifier 300 used in the presently preferred embodiment of the invention is a binary decision tree made up of discriminant functions and/or thresholds that can separate the two groups of cells. Once the classifier has been constructed, the classifier is fed with the feature values 306 that are obtained by imaging cells obtained from a patient whose condition is unknown. The classifier provides a determination 308 of whether the nuclei exhibit MACs or not.

Figure 10:
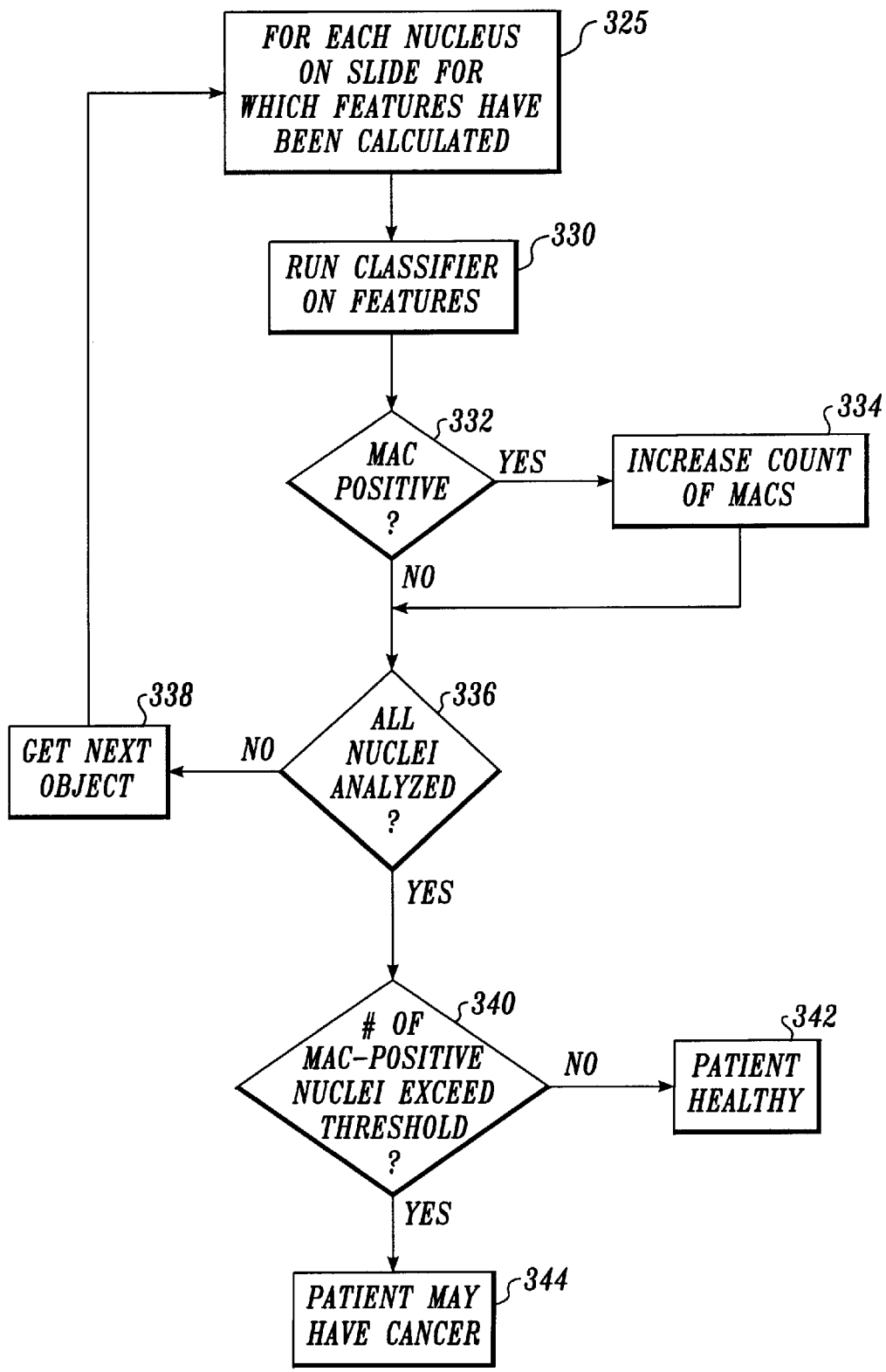
FIG. 10 is a flow chart of the steps performed by the present invention to determine whether a patient is normal or abnormal based on the presence of MACs.

FIG. 10 is a flow chart of the steps performed by the present invention to determine whether a patient potentially has cancer. Beginning at a step 325, the computer system recalls the features calculated for each in-focus nuclei on the slide. At a step 330, the computer system runs the classifier that identifies MACs based on these features. At a step 332, the computer system provides an indication of whether the nucleus in question is MAC-positive or not. If the answer to step 332 is yes, then an accumulator that totals the number of MAC-positive nuclei for the slide is increased at a step 334. At a step 336, the computer system determines whether all the nuclei for which features have been calculated have been analyzed. If not, the next set of features is recalled at step 338 and the process repeats itself. At a step 340, the computer system determines whether the frequency of MAC-positive cells on the slide exceeds a predetermined threshold. For example, in a particular preparation of cells (air dried, as is the practice in British Columbia, Canada) to detect cervical cancer, it has been determined that if the total number of MAC-positive epithelial cells divided by the total number of epithelial cells analyzed exceeds 0.45 per slide, then there is an 85% chance that the patient has or will develop cancer. If the frequency of cells exhibiting MACs exceeds the threshold, the computer system can indicate that the patient is healthy at step 342 or likely has or will develop cancer at step 344.

The threshold above which it is likely that a patient exhibiting MACs has or will develop cancer is determined by comparing the MAC scores of a large numbers of patients who did develop cancer and those who did not. As will be appreciated by those skilled in the art, the particular threshold used will depend on the type of cancer to be detected, the equipment used to image the cells, etc.

The MAC detection system of the present invention can also be used to determine the efficacy of cancer treatment. For example, patients who have had a portion of a lung removed as a treatment for lung cancer can be asked to provide a sample of apparently normal cells taken from the remaining lung tissue. If a strong MAC presence is detected, there is a high probability that the cancer will return. Conversely, the inventors have found that the number of MAC cells decreases when a cancer treatment is effective.

As described above, the ability of the present invention to detect malignancy-associated changes depends on the values of the features computed. The following is a list of the features that is currently calculated for each in-focus object.

I.2 Coordinate Systems, Jargon and Notation

Each image is a rectangular array of square pixels that contains within it the image of an (irregularly shaped) object, surrounded by background. Each pixel $P_{ij}$ is an integer representing the photometric value (gray scale) of a corresponding small segment of the image, and may range from 0 (completely opaque) to 255 (completely transparent). The image rectangle is larger than the smallest rectangle that can completely contain the object by at least two rows, top and bottom, and two columns left and right, ensuring that background exists all around the object. The rectangular image is a matrix of pixels, $P_{ij}$, spanning i=1, L columns and j=1, M rows and with the upper left-hand pixel as the coordinate system origin, i=j=1.

The region of the image that is the object is denoted by its characteristic function, $\Omega$; this is also sometimes called the "object mask" or, simply, the "mask." For some features, it makes sense to dilate the object mask by one pixel all around the object; this mask is denoted $\Omega^+$. Similarly, an eroded mask is denoted $\Omega^-$. The object mask is a binary function:

$$\Omega = (\Omega_{1,1}, \Omega_{1,2}, \ldots \Omega_{i,j}, \ldots \Omega_{L,M}) \quad (1)$$

where $$\Omega_{i,j} = \begin{cases} 1 & \text{if } (i, j) \in \text{object} \\ 0 & \text{if } (i, j) \notin \text{object} \end{cases}$$

and where "(i,j) $\in$ object" means pixels at coordinates: (i, j) are part of the object, and "(i,j) $\notin$ object" means pixels at coordinates: (i, j) are not part of the object.

II Morphological Features

Morphological features estimate the image area, shape, and boundary variations of the object.

II.1 Area

The area, A, is defined as the total number of pixels belonging to the object, as defined by the mask, $\Omega$:

$$\text{area} = A = \sum_{i=1}^{L} \sum_{j=1}^{M} \Omega_{ij} \quad (2)$$

where i, j and $\Omega$ are defined in Section I.2 above.

II.2 x_centroid, y_centroid

The x_centroid and y_centroid are the coordinates of the geometrical center of the object, defined with respect to the image origin (upper-left hand corner):

$$\text{x\_centroid} = \frac{\sum_{i=1}^{L} \sum_{j=1}^{M} i \cdot \Omega_{i,j}}{A} \quad (3)$$

$$\text{y\_centroid} = \frac{\sum_{i=1}^{L} \sum_{j=1}^{M} i \cdot \Omega_{i,j}}{A} \quad (4)$$

where i and j are the image pixel coordinates and $\Omega$ is the object mask, as defined in Section 1.2 above, and A is the object area.

II.3 mean_radius, max_radius

The mean_radius and max_radius features are the mean and maximum values of the length of the object's radial vectors from the object centroid to its 8 connected edge pixels:

$$\text{mean\_radius} = \bar{r} = \frac{\sum_{k=1}^{N} r_k}{N} \quad (5)$$

$$\text{max\_radius} = \max(r_k) \quad (6)$$

where $r_k$ is the $k^{th}$ radial vector, and N is the number of 8 connected pixels on the object edge.

II.4 var_radius

The var_radius feature is the variance of length of the object's radius vectors, as defined in Section II.3.

$$\text{var\_radius} = \frac{\sum_{k=1}^{N} (r_k - \bar{r})^2}{N - 1} \quad (7)$$

where $r_k$ is the $k^{th}$ radius vector, $\bar{r}$ is the mean_radius, and N is the number of 8 connected edge pixels.

II.5 Sphericity

The sphericity feature is a shape measure, calculated as a ratio of the radii of two circles centered at the object centroid (defined in Section II.2 above). One circle is the largest circle that is fully inscribed inside the object perimeter, corresponding to the absolute minimum length of the object's radial vectors. The other circle is the minimum circle that completely circumscribes the object's perimeter, corresponding to the absolute maximum length of the object's radial vectors. The maximum sphericity value: 1 is given for a circular object:

$$\text{sphericity} = \frac{\text{min\_radius}}{\text{max\_radius}} = \frac{\min(r_k)}{\max(r_k)} \quad (8)$$

where $r_k$ is the $k^{th}$ radius vector.

II.6 Eccentricity

The eccentricity feature is a shape function calculated as the square root of the ratio of maximal and minimal eigenvalues of the second central moment matrix of the object's characteristic function, $\Omega$:

$$\text{eccentricity} = \sqrt{\frac{\lambda_1}{\lambda_2}} \quad (9)$$

where $\lambda_1$ and $\lambda_2$ are the maximal and minimal eigenvalues, respectively, and the characteristic function, $\Omega$, as given by Equation 1. The second central moment matrix is calculated as:

$$\begin{bmatrix} x_{moment2} & xy_{crossmoment2} \\ xy_{crossmoment2} & y_{moment2} \end{bmatrix} = \quad (10)$$

$$\begin{bmatrix} \sum_{i=1}^{L}\sum_{j=1}^{M}\left(i - \frac{\sum_{i=1}^{L} i \cdot \Omega_{i,j}}{L}\right) & \sum_{i=1}^{L}\sum_{j=1}^{M}\left(i - \frac{\sum_{i=1}^{L} i \cdot \Omega_{i,j}}{L}\right)\left(j - \frac{\sum_{j=1}^{M} j \cdot \Omega_{i,j}}{M}\right) \\ \sum_{i=1}^{L}\sum_{j=1}^{M}\left(i - \frac{\sum_{i=1}^{L} i \cdot \Omega_{i,j}}{L}\right)\left(j - \frac{\sum_{j=1}^{M} j \cdot \Omega_{i,j}}{M}\right) & \sum_{i=1}^{L}\sum_{j=1}^{M}\left(j - \frac{\sum_{j=1}^{M} j \cdot \Omega_{i,j}}{M}\right)^2 \end{bmatrix}$$

g,19

Eccentricity may be interpreted as the ratio of the major axis to minor axis of the "best fit" ellipse which describes the object, and gives the minimal value 1 for circles.

II.7 inertia_shape

The inertia shape feature is a measure of the "roundness" of an object calculated as the moment of inertia of the object mask, normalized by the area squared, to give the minimal value 1 for circles:

$$\text{inertia\_shape} = \frac{2\pi \sum_{i=1}^{L}\sum_{j=1}^{M} R_{i,j}^2 \Omega_{i,j}}{A^2} \quad (11)$$

where $R_{i,j}$ is the distance of the pixel, $P_{i,j}$, to the object centroid (defined in Section II.2), and A is the object area, and $\Omega$ is the mask defined by Equation 1.

II.8 Compactness

The compactness feature is another measure of the object's "roundness." It is calculated as the perimeter squared divided by the object area, giving the minimal value 1 for circles:

$$\text{compactness} = \frac{P^2}{4\pi A} \quad (12)$$

where P is the object perimeter and A is the object area. Perimeter is calculated from boundary pixels (which are themselves 8 connected) by considering their 4 connected neighborhood:

$$P = N_1 + \sqrt{2}N_2 + 2N_3 \quad (13)$$

where $N_1$ is the number of pixels on the edge with 1 non-object neighbor, $N_2$ is the number of pixels on the edge with 2 non-object neighbors, and $N_3$ is the number of pixels on the edge with 3 non-object neighbors.

II.9 cell_orient

The cell_orient feature represents the object orientation measured as a deflection of the main axis of the object from they direction:

$$\text{cell\_orient} = \frac{180}{\pi}\left(\frac{\pi}{2} + \arctan\left[\frac{(\lambda_1 - y_{moment2})}{xy_{cross\_moment2}}\right]\right) \quad (14)$$

where $y_{moment2}$ and $xy_{crossmoment2}$ are the second central moments of the characteristic function $\Omega$ defined by Equation 1 above, and $\lambda_1$ is the maximal eigenvalue of the second central moment matrix of that function (see Section II.6 above). The main axis of the object is defined by the eigenvector corresponding to the maximal eigenvalue. A geometrical interpretation of the cell_orient is that it is the angle (measured in a clockwise sense) between the y axis and the "best fit" ellipse major axis.

For slides of cell suspensions, this feature should be meaningless, as there should not be any a priori preferred cellular orientation. For histological sections, and possibly smears, this feature may have value. In smears, for example, debris may be preferentially elongated along the slide long axis.

II.10 Elongation

Features in Sections II.10 to II.13 are calculated by sweeping the radius vector (from the object centroid, as defined in Section II.2, to object perimeter) through 128 discrete equal steps (i.e., an angle of $2\pi/128$ per step), starting at the top left-most object edge pixel, and sweeping in a clockwise direction. The function is interpolated from an average of the object edge pixel locations at each of the 128 angles.

The elongation feature is another measure of the extent of the object along the principal direction (corresponding to the major axis) versus the direction normal to it.

These lengths are estimated using Fourier Transform coefficients of the radial function of the object:

$$\text{elongation} = \frac{a_0 + 2\sqrt{a_2^2 + b_2^2}}{a_0 - 2\sqrt{a_2^2 + b_2^2}} \quad (15)$$

where $a_2, b_2$, are Fourier Transform coefficients of the radial function of the object, $r(\theta)$, defined by:

$$r(\theta) = \frac{a_0}{2} + \sum_{n=1}^{m} a_n \cos(n\theta) + \sum_{n=1}^{m} b_n \sin(n\theta) \quad (16)$$

II.11 freq_low_fft

The freq_low_fft gives an estimate of coarse boundary variation, measured as the energy of the lower harmonics of the Fourier spectrum of the object's radial function (from 3rd to 11th harmonics):

$$\text{freq\_low\_fft} = \sum_{n=3}^{11} (a_n^2 + b_n^2) \quad (17)$$

where $a_n, b_n$ are Fourier Transform coefficients of the radial function, defined in Equation 16.

II.12 freq_high_fft

The freq_high_fft gives an estimate of the fine boundary variation, measured as the energy of the high frequency Fourier spectrum (from 12th to 32nd harmonics) of the object's radial function:

$$\text{freq\_high\_fft} = \sum_{n=12}^{32} (a_n^2 + b_n^2) \quad (18)$$

where $a_n, b_n$ are Fourier Transform coefficients of the $n^{th}$ harmonic, defined by Equation 16.

II.13 harmon01_fft, ..., harmon32_fft

The harmon01_fft, ... harmon32_fft features are estimates of boundary variation, calculated as the magnitude of the Fourier Transform coefficients of the object radial function for each harmonic 1–32:

$$\text{harmon } n\_fft = \sqrt{a_n^2 + b_n^2} \quad (19)$$

where $a_n, b_n$ are Fourier Transform coefficients of the $n^{th}$ harmonic, defined by Equation 16.

III Photometric Features

Photometric features give estimations of absolute intensity and optical density levels of the object, as well as their distribution characteristics.

III.1 DNA_Amount

DNA_Amount is the "raw" (unnormalized) measure of the integrated optical density of the object, defined by a once dilated mask, $\Omega^+$:

$$\text{DNA\_Amount} = \sum_{i=1}^{L} \sum_{j=1}^{M} OD_{i,j} \Omega_{i,j}^+ \quad (20)$$

where the once dilated mask, $\Omega^+$ is defined in Section I.2 and OD is the optical density, calculated according to [12]:

$$OD_{i,j} = \log_{10} I_B - \log_{10} I_{i,j} \quad (21)$$

where $I_B$ is the intensity of the local background, and $I_{i,j}$ is the intensity of the i,j th pixel.

III.2 DNA_Index

DNA_Index is the normalized measure of the integrated optical density of the object:

$$\text{DNA\_Index} = \frac{\text{DNA\_Amount}}{iod_{norm}} \quad (22)$$

where $iod_{norm}$ is the mean value of the DNA amount for a particular object population from the slide (e.g., leukocytes).

III.3 var_intensity, mean_intensity

The var_intensity and mean_intensity features are the variance and mean of the intensity function of the object, I, defined by the mask, $\Omega$:

$$\text{var\_intensity} = \frac{\sum_{i=1}^{L} \sum_{j=1}^{M} (I_{i,j} \Omega_{i,j} - \bar{I})^2}{A - 1} \quad (23)$$

where A is the object area, $\Omega$ is the object mask defined in Equation 1, and $\bar{I}$ is given by:

$$\bar{I} = \frac{\sum_{i=1}^{L} \sum_{j=1}^{M} I_{i,j} \Omega_{i,j}}{A} \quad (24)$$

$\bar{I}$ is the "raw" (unnormalized) mean intensity. mean intensity is normalized against $iod_{norm}$ defined in Section III.2:

$$\text{mean\_intensity} = \bar{I} \frac{(iod_{norm})}{100} \quad (25)$$

III.4 OD_maximum

OD_maximum is the largest value of the optical density of the object, normalized to $iod_{norm}$, as defined in Section III.2 above:

$$\text{OD\_maximum} = \max(OD_{i,j}) \left( \frac{100}{iod_{norm}} \right) \quad (26)$$

III.5 OD_variance

OD_variance is the normalized variance (second moment) of optical density function of the object:

$$\text{OD\_variance} = \frac{\sum_{i=1}^{L} \sum_{j=1}^{M} (OD_{i,j} \Omega_{i,j} - \overline{OD})^2}{(A - 1)\overline{OD}^2} \quad (27)$$

where $\Omega$ is the object mask as defined in Section 1.2, $\overline{OD}$ is the mean value of the optical density of the object:

$$\overline{OD} = \left( \frac{\sum_{i=1}^{L} \sum_{j=1}^{M} OD_{i,j} \Omega_{i,j}}{A} \right)$$

and A is the object area (total number of pixels). The variance is divided by the square of the mean optical density in order to make the measurement independent of the staining intensity of the cell.

III.6 OD_skewness

The OD_skewness feature is the normalized third moment of the optical density function of the object:

$$\text{OD\_skewness} = \frac{\sum_{i=1}^{L} \sum_{j=1}^{M} (OD_{i,j} \Omega_{i,j} - \overline{OD})^3}{(A - 1)\left( \sum_{i=1}^{L} \sum_{j=1}^{M} (OD_{i,j} \Omega_{i,j} - \overline{OD})^2 \right)^{\frac{3}{2}}} \quad (28)$$

where $\Omega$ is the object mask as defined in Section 1.2, $\overline{OD}$ is the mean value of the optical density of the object and A is the object area (total number of pixels).

III.7 OD_kurtosis

OD_kurtosis is the normalized fourth moment of the optical density function of the object:

$$OD\_kurtosis = \frac{\sum_{i=1}^{L}\sum_{j=1}^{M}(OD_{i,j}\Omega_{i,j} - \overline{OD})^4}{(A-1)\left(\sum_{i=1}^{L}\sum_{j=1}^{M}(OD_{i,j}\Omega_{i,j} - \overline{OD})^2\right)^2} \quad (29)$$

where $\Omega$ is the object mask as defined in Section 1.2, $\overline{OD}$ is the mean value of the optical density of the object and A is the object area.

IV Discrete Texture Features

The discrete texture features are based on segmentation of the object into regions of low, medium and high optical density. This segmentation of the object into low, medium and high density regions is based on two thresholds: optical density high threshold and optical density medium threshold. These thresholds are scaled to the sample's $iod_{norm}$ value, based on the DNA amount of a particular subset of objects (e.g., lymphocytes), as described in Section III.2 above.

By default, these thresholds have been selected such that the condensed chromatin in leukocytes is high optical density material. The second threshold is located half way between the high threshold and zero.

The default settings from which these thresholds are calculated are stored in the computer as:

CHROMATIN_HIGH_THRES=36

CHROMATIN_MEDIUM_THRES=18

$A^{high}$ is the area of the pixels having an optical density between 0 and 18, $A^{med.}$ is the area of the pixels having an optical density between 18 and 36 and $A^{low}$ is the area of the pixels having an optical density greater than 36. Together the areas $A^{high}$, $A^{med}$ and $A^{low}$ sum to the total area of the object. The actual thresholds used are these parameters, divided by 100, and multiplied by the factor $iod_{norm}/100$.

In the following discussion, $\Omega^{low}$, $\Omega^{med}$, and $\Omega^{high}$ are masks for low-, medium-, and high-optical density regions of the object, respectively, defined in analogy to Equation 1.

IV.1 lowDNAarea, medDNAarea, hiDNAarea

These discrete texture features represent the ratio of the area of low, medium, and high optical density regions of the object to the total object area:

$$lowDNAarea = \frac{\sum_{i=1}^{L}\sum_{j=1}^{M}\Omega_{i,j}^{low}}{\sum_{i=1}^{L}\sum_{j=1}^{M}\Omega_{i,j}} = \frac{A^{low}}{A} \quad (30)$$

$$medDNAarea = \frac{\sum_{i=1}^{L}\sum_{j=1}^{M}\Omega_{i,j}^{med}}{\sum_{i=1}^{L}\sum_{j=1}^{M}\Omega_{i,j}} = \frac{A^{med}}{A} \quad (31)$$

$$hiDNAarea = \frac{\sum_{i=1}^{L}\sum_{j=1}^{M}\Omega_{i,j}^{hi}}{\sum_{i=1}^{L}\sum_{j=1}^{M}\Omega_{i,j}} = \frac{A^{hi}}{A} \quad (32)$$

where $\Omega$ is the object mask as defined in Equation 1, and A is the object area.

IV.2 lowDNAamnt, medDNAamnt, hiDNAamnt

These discrete texture features represent the total extinction ratio for low, medium, and high optical density regions of the object, calculated as the value of the integrated optical density of the low-, medium-, and high-density regions, respectively, divided by the total integrated optical density:

$$lowDNAamnt = \frac{\sum_{i=1}^{L}\sum_{j=1}^{M}OD_{i,j}\Omega_{i,j}^{low}}{\sum_{i=1}^{L}\sum_{j=1}^{M}OD_{i,j}\Omega_{i,j}} \quad (33)$$

$$medDNAamnt = \frac{\sum_{i=1}^{L}\sum_{j=1}^{M}OD_{i,j}\Omega_{i,j}^{med}}{\sum_{i=1}^{L}\sum_{j=1}^{M}OD_{i,j}\Omega_{i,j}} \quad (34)$$

$$hiDNAamnt = \frac{\sum_{i=1}^{L}\sum_{j=1}^{M}OD_{i,j}\Omega_{i,j}^{hi}}{\sum_{i=1}^{L}\sum_{j=1}^{M}OD_{i,j}\Omega_{i,j}} \quad (35)$$

where $\Omega$ is the object mask as defined in Equation 1, and OD is the optical density as defined by Equation 21.

IV.3 lowDNAcomp, medDNAcomp, hiDNAcomp, mhDNAcomp

These discrete texture features are characteristic of the compactness of low-, medium-, high-, and combined medium- and high-density regions, respectively, treated as single (possibly disconnected) objects. They are calculated as the perimeter squared of each region, divided by $4\pi$ (area) of the region.

$$lowDNAcomp = \frac{(P^{low})^2}{4\pi A^{low}} \quad (36)$$

$$medDNAcomp = \frac{(P^{med})^2}{4\pi A^{med}} \quad (37)$$

$$hiDNAcomp = \frac{(P^{hi})^2}{4\pi A^{hi}} \quad (38)$$

$$mhDNAcomp = \frac{(P_{med} + P_{hi})^2}{4\pi(A^{med} + A^{hi})} \quad (39)$$

where P is the perimeter of each of the optical density regions, defined in analogy to Equation 13, and A is the region area, defined in analogy to Equation 2.

IV.4 low_av_dst, med_av_dst, hi_av_dst, mh_av_dst

These discrete texture features represent the average separation between the low-, medium-, high-, and combined medium- and high-density pixels from the center of the object, normalized by the object mean_radius.

$$low\_av\_dst = \frac{\sum_{i=1}^{L}\sum_{j=1}^{M}R_{i,j}\Omega_{i,j}^{low}}{A^{low} \cdot mean\_radius} \quad (40)$$

$$med\_av\_dst = \frac{\sum_{i=1}^{L}\sum_{j=1}^{M}R_{i,j}\Omega_{i,j}^{med}}{A^{med} \cdot mean\_radius} \quad (41)$$

-continued $$hi\_av\_dst = \frac{\sum_{i=1}^{L}\sum_{j=1}^{M} R_{i,j}\Omega_{i,j}^{hi}}{A^{hi} \cdot mean\_radius} \quad (42)$$

$$mh\_av\_dst = \frac{\sum_{i=1}^{L}\sum_{j=1}^{M} R_{i,j}\Omega_{i,j}^{med} + \sum_{i=1}^{L}\sum_{j=1}^{M} R_{i,j}\Omega_{i,j}^{hi}}{(A^{med} + A^{hi}) \cdot mean\_radius} \quad (43)$$

where $R_{i,j}$ is defined in Section II.7 as the distance from pixel $P_{i,j}$ to the object centroid (defined in Section II.2), and the object mean_radius is defined by Equation 5.

IV.5 lowVSmed_DNA, lowVShigh_DNA, lowVSmh_DNA

These discrete texture features represent the average extinction ratios of the low-density regions, normalized by the medium-, high-, and combined medium- and high-average extinction values, respectively. They are calculated as the mean optical density of the medium-, high-, and combined medium- and high-density clusters divided by the mean optical density of the low density clusters.

$$lowVSmed\_DNA = \left(\frac{\sum_{i=1}^{L}\sum_{j=1}^{M} OD_{i,j}\Omega_{i,j}^{med}}{A^{med}}\right) \div \left(\frac{\sum_{i=1}^{L}\sum_{j=1}^{M} OD_{i,j}\Omega_{i,j}^{low}}{A^{low}}\right) \quad (44)$$

$$lowVShi\_DNA = \left(\frac{\sum_{i=1}^{L}\sum_{j=1}^{M} OD_{i,j}\Omega_{i,j}^{hi}}{A^{hi}}\right) \div \left(\frac{\sum_{i=1}^{L}\sum_{j=1}^{M} OD_{i,j}\Omega_{i,j}^{low}}{A^{low}}\right) \quad (45)$$

$$lowVSmed\_DNA = \quad (46)$$
$$\left(\frac{\sum_{i=1}^{L}\sum_{j=1}^{M} OD_{i,j}\Omega_{i,j}^{med} + \sum_{i=1}^{L}\sum_{j=1}^{M} OD_{i,j}\Omega_{i,j}^{hi}}{A^{med} + A^{hi}}\right) \div \left(\frac{\sum_{i=1}^{L}\sum_{j=1}^{M} OD_{i,j}\Omega_{i,j}^{low}}{A^{low}}\right)$$

where OD is the region optical density defined in analogy to Equation 21, $\Omega$ is the region mask, defined in analogy to Equation 1, and A is the region area, defined in analogy to Equation 2.

IV.6 low_den_obj, med_den_obj, high_den_obj

These discrete texture features are the numbers of discrete 8-connected subcomponents of the objects consisting of more than one pixel of low, medium, and high density.

IV.7 low_cntr_mass, med_cntr_mass, high_cntr_mass

These discrete texture features represent the separation between the geometric center of the low, medium, and high optical density clusters (treated as if they were single objects) and the geometric center of the whole object, normalized by its mean_radius.

$$low\_cntr\_mass = \left[\left(\frac{\sum_{i=1}^{L}\sum_{j=1}^{M} i \cdot \Omega_{i,j}^{low}}{A^{low}} - x\_centroid\right)^2 + \right. \quad (47)$$
$$\left. \left(\frac{\sum_{i=1}^{L}\sum_{j=1}^{M} j \cdot \Omega_{i,j}^{low}}{A^{low}} - y\_centroid\right)^2\right]^{\frac{1}{2}} \div$$
$$(mean\_radius)$$

$$med\_cntr\_mass = \left[\left(\frac{\sum_{i=1}^{L}\sum_{j=1}^{M} i \cdot \Omega_{i,j}^{med}}{A^{med}} - x\_centroid\right)^2 + \right. \quad (48)$$
$$\left. \left(\frac{\sum_{i=1}^{L}\sum_{j=1}^{M} j \cdot \Omega_{i,j}^{med}}{A^{med}} - y\_centroid\right)^2\right]^{\frac{1}{2}} \div$$
$$(mean\_radius)$$

$$hi\_cntr\_mass = \left[\left(\frac{\sum_{i=1}^{L}\sum_{j=1}^{M} i \cdot \Omega_{i,j}^{hi}}{A^{hi}} - x\_centroid\right)^2 + \right. \quad (49)$$
$$\left. \left(\frac{\sum_{i=1}^{L}\sum_{j=1}^{M} j \cdot \Omega_{i,j}^{hi}}{A^{hi}} - y\_centroid\right)^2\right]^{\frac{1}{2}} \div$$
$$(mean\_radius)$$

where mean_radius of the object is defined by Equation 5, the object's centroid is defined in Section II.2, $\Omega$ is the region mask defined in analogy to Equation 1, and A is the region area defined in analogy to Equation 2.

V Markovian Texture Features

Markovian texture features are defined from the co-occurrence matrix, $\Delta_{\lambda,\mu}$ of object pixels. Each element of that matrix stands for the conditional probability of the pixel of grey level $\lambda$ occurring next (via 8-connectedness) to a pixel of grey level $\mu$, where $\lambda,\mu$ are row and column indices of the matrix, respectively. However, the computational algorithms used here for the calculation of Markovian texture features uses so-called sum and difference histograms: $H_l^s$ and $H_m^d$, where $H_l^s$ is the probability of neighboring pixels having grey levels which sum to 1, and $H_m^d$ is the probability of neighboring pixels having grey level differences of m, where an 8-connected neighborhood is assumed. Values of grey levels, 1, m, used in the sum and difference histogram are obtained by quantization of the dynamic range of each individual object into 40 levels.

For completeness, the formulae that follow for Markovian texture features include both the conventional formulae and the computational formulae actually used.

V.1 Entropy

The entropy feature represents a measure of "disorder" in object grey level organization: large values correspond to very disorganized distributions, such as a "salt and pepper" random field:

$$entropy = \sum_{\lambda}\sum_{\mu} \Delta_{\lambda,\mu} \log_{10} \Delta_{\lambda,\mu} \quad (conventional) \quad (50)$$

$$entropy = -\sum_{l} H_l^s \log_{10} H_l^s - \sum_{m} H_m^d \log_{10} H_m^d \quad (computational)$$

V.2 Energy

The energy feature gives large values for an object with a spatially organized grey scale distribution. It is the opposite of entropy, giving large values to an object with large regions of constant grey level:

$$\text{energy} = \sum_\lambda \sum_\mu \Delta^2_{\lambda,\mu} \quad \text{(conventional)} \qquad (51)$$

$$\text{energy} = \sum_l (H_l^s) + \sum_m (H_m^d)^2 \quad \text{(computational)}$$

V.3 Contrast

The contrast feature gives large values for an object with frequent large grey scale variations:

$$\text{contrast} = \sum_\lambda \sum_\mu (\lambda - \mu)^2 \Delta_{\lambda,\mu} \quad \text{(conventional)} \qquad (52)$$

$$\text{contrast} = \sum_m m^2 H_m^d \quad \text{(computational)}$$

V.4 Correlation

A large value for correlation indicates an object with large connected subcomponents of constant grey level and with large grey level differences between adjacent components:

$$\text{correlation} = \sum_\lambda \sum_\mu (\lambda - \overline{I^q})(\mu - \overline{I^q}) \Delta_{\lambda,\mu} \quad \text{(conventional)} \qquad (53)$$

$$\text{correlation} = \frac{1}{2}\left(\sum_\lambda (l - 2\overline{I^q}) H_l^s - \sum_m m^2 H_m^d\right) \quad \text{(computational)}$$

where $\overline{I^q}$ is the mean intensity of the object calculated for the grey scale quantized to 40 levels.

V.5 Homogeneity

The homogeneity feature is large for objects with slight and spatially smooth grey level variations:

$$\text{homogeneity} = \sum_\lambda \sum_\mu \frac{1}{1 + (\lambda - \mu)^2} \Delta_{\lambda,\mu} \quad \text{(conventional)} \qquad (54)$$

$$\text{homogeneity} = \sum_m \frac{1}{(1 + m)^2} H_m^d \quad \text{(computational)}$$

V.6 cl_shade

The cl_shade feature gives large absolute values for objects with a few distinct clumps of uniform intensity having large contrast with the rest of the object. Negative values correspond to dark clumps against a light background while positive values indicate light clumps against a dark background:

$$\text{cl\_shade} = \sum_\lambda \sum_\mu (\lambda + \mu - 2\overline{I^q})^3 \Delta_{\lambda,\mu} \quad \text{(conventional)} \qquad (55)$$

$$\text{cl\_shade} = \frac{\sum_l (l - 2\overline{I^q})^3 H_l^s}{\left(\sum_l (l - 2\overline{I^q})^2 H_l^s\right)^{\frac{3}{2}}} \quad \text{(computational)}$$

V.7 cl_prominence

The feature cl_prominence measures the darkness of clusters.

$$\text{cl\_prominence} = \sum_\lambda \sum_\mu (\lambda + \mu - 2\overline{I^q})^4 \Delta_{\lambda,\mu} \quad \text{(conventional)} \qquad (56)$$

-continued $$\text{cl\_prominence} = \frac{\sum_l (l - 2\overline{I^q})^4 H_l^s}{\left(\sum_l (l - 2\overline{I^q})^2 H_l^s\right)^2} \quad \text{(computational)}$$

VI Non-Markovian Texture Features

These features describe texture in terms of global estimation of grey level differences of the object.

VI.1 den_lit_spot, den_drk_spot

These are the numbers of local maxima and local minima, respectively, of the object intensity function based on the image averaged by a 3×3 window, and divided by the object area.

$$\text{den\_lit\_spot} = \frac{\sum_{i'=1}^{L} \sum_{j'=1}^{M} \delta_{i',j'}^{\max}}{A} \qquad (57)$$

and $$\text{den\_drk\_spot} = \frac{\sum_{i'=1}^{L} \sum_{j'=1}^{M} \delta_{i',j'}^{\min}}{A} \qquad (58)$$

where $$\delta_{i',j'}^{\max} = \begin{cases} 1 & \text{if there exists a local maximum of } I'_{i',j'}, \text{ with value } \max_{i',j'} \\ 0 & \text{otherwise} \end{cases}$$

and $$\delta_{i',j'}^{\min} = \begin{cases} 1 & \text{if there exists a local minimum of } I'_{i',j'}, \text{ with value } \min_{i',j'} \\ 0 & \text{otherwise} \end{cases}$$

and where $$I'_{i',j'} = \frac{1}{9} \sum_{i=i'-1}^{i'+1} \sum_{j=j'-1}^{j'+1} I_{i,j} \Omega_{i,j}$$

and I is the object intensity, $\Omega$ is the object mask, and A is the object area.

VI.2 range_extreme

This is the intensity difference between the largest local maximum and the smallest local minimum of the object intensity function, normalized against the slide DNA amount, $iod_{norm}$, defined in Section III.2. The local maxima, $\max_{i',j'}$, and minima, $\min_{i',j'}$, are those in Section VI.1 above.

$$\text{range\_extreme} = \left(\max(\max_{i',j'}) - (\min(\min_{i,j}))\right)\left(\frac{100}{iod_{norm}}\right) \qquad (59)$$

VI.3 range_average

This is the intensity difference between the average intensity of the local maxima and the average intensity of the local minima, normalized against the slide DNA amount value, $iod_{norm}$, defined in Section III.2 above. The local maxima, $\max_{i',j'}$ and minima, $\min_{i',j'}$, values used are those from Section VI.1 above.

$$\text{range\_average} = \left( \frac{\sum_{i'=1}^{L}\sum_{j'=1}^{M} \max_{i',j'}}{\sum_{i'=1}^{L}\sum_{j'=1}^{M} \delta_{i',j'}^{\max}} - \frac{\sum_{i'=1}^{L}\sum_{j'=1}^{M} \min_{i',j'}}{\sum_{i'=1}^{L}\sum_{j'=1}^{M} \delta_{i',j'}^{\min}} \right) \frac{100}{iod_{norm}} \quad (60)$$

VI.4 center_of_13 gravity

The center_of_gravity feature represents the distance from the geometrical center of the object to the "center of mass" of the optical density function, normalized by the mean_radius of the object:

$$\text{center\_of\_gravity} = \frac{\left[ \left( \frac{\sum_{i=1}^{L}\sum_{j=1}^{M} i \cdot OD_{i,j} \Omega_{i,j}}{\sum_{i=1}^{L}\sum_{j=1}^{M} OD_{i,j} \Omega_{i,j}} - x\_centroid \right)^2 + \left( \frac{\sum_{i=1}^{L}\sum_{j=1}^{M} j \cdot OD_{i,j} \Omega_{i,j}}{\sum_{i=1}^{L}\sum_{j=1}^{M} OD_{i,j} \Omega_{i,j}} - y\_centroid \right)^2 \right]}{\text{mean\_radius}} \quad (61)$$

This gives a measure of the nonuniformity of the OD distribution.

VII Fractal Texture Features

The fractal texture features are based on the area of the three-dimensional surface of the object's optical density represented essentially as a three-dimensional bar graph, with the vertical axis representing optical density, and the horizontal axes representing the x and y spatial coordinates. Thus, each pixel is assigned a unit area in the x-y plane plus the area of the sides of the three-dimensional structure proportional to the change in the pixel optical density with respect to its neighbors. The largest values of fractal areas correspond to large objects containing small subcomponents with high optical density variations between them.

The difference between fractal1_area and fractal2_area is that these features are calculated on different scales: the second one is based on an image in which four pixels are averaged into a single pixel, thereby representing a change of scale of fractal1_area. This calculation needs the additional mask transformation: $\Omega_{i2,j2}$ represents the original mask $\Omega$ with 4 pixels mapped into one pixel and any square of 4 pixels not completely consisting of object pixels is set to zero. $\Omega i,j$ represents $\Omega_{i2,j2}$ expanded by 4 so that each pixel in $\Omega_{i2,j2}$ is 4 pixels in $\Omega i,j$.

VII.1 fractal1_area $$\text{fractal1\_area} = \sum_{i=2}^{L}\sum_{j=2}^{M} (|OD_{i,j}^* - OD_{i,j-1}^*| + |OD_{i,j}^* - OD_{i-1,j}^*| + 1)\Omega_{i,j} \quad (62)$$

where $OD_{i,j}^*$ is the optical density function of the image scaled by a factor common to all images such that the possible optical density values span 256 levels.

VII.2 fractal2_area

This is another fractal dimension, but based on an image in which four pixel squares are averaged into single pixels, thereby representing a change of scale of fractal1_area in Section VII.1 above.

$$\text{fractal2\_area} = \sum_{i_2=2}^{L_2}\sum_{j_2=2}^{M_2} (|OD_{i2,j2}^* - OD_{i_2,j_2-1}^*| + |OD_{i2,j2}^* - OD_{i_2-1,j_2}^*| + 1)\Omega_{i_2,j_2} \quad (63)$$

where, $$L_2 = \left[\frac{L}{2}\right], M_2 = \left[\frac{M}{2}\right],$$

with $L_2$, $M_2$ as integers, and OD $$OD_{i2,j2}^*$$

is a scaled optical density function of the image, with 4 pixels averaged into one.

VII.3 fractal_dimen

The fractal_dimen feature is calculated as the difference between logarithms of fractal1_area and fractal2_area, divided by log 2. This varies from 2 to 3 and gives a measure of the "fractal behavior" of the image, associated with a rate at which measured surface area increases at finer and finer scales.

$$\text{fractal\_dimen} = \frac{\log_{10}(\text{fractal1\_area}) - \log_{10}(\text{fractal2\_area})}{\log_{10} 2} \quad (64)$$

VIII Run Length Texture Features

Run length features describe texture in terms of grey level runs, representing sets of consecutive, collinear pixels having the same grey level value. The length of the run is the number of pixels in the run. These features are calculated over the image with intensity function values transformed into 8 levels.

The run length texture features are defined using grey level length matrices, $\mathfrak{R}_{p,q}^{\Theta}$ for each of the four principal directions: $\Theta=0°$, $45°$, $90°$, $135°$, where the directions are defined clockwise with respect to the positive x-axis. Note: As defined here, the run length texture features are not rotationally invariant, and therefore cannot, in general, be used separately since for most samples there, will be no a priori preferred direction for texture. For example, for one cell, a run length feature may be oriented at 45°, but at 90° in the next; in general, these are completely equivalent. Each element of matrix $\mathfrak{R}_{p,q}^{\Theta}$ specifies the number of times that the object contains a run of length q, in a given direction, $\Theta$, consisting of pixels lying in grey level range, p (out of 8 grey levels). Let $N^g=8$ be the number of grey levels, and $N^r$ be the number of different run lengths that occur in the object; then the run length features are described as follows:

VIII.1 short0_runs, short45_runs, short90_runs, short135_runs

These give large values for objects in which short runs, oriented at 0°, 45°, 90°, or 135°, dominate.

$$\text{short}\theta\_\text{runs} = \frac{\sum_{p=1}^{N^g}\sum_{q=1}^{N^r} \frac{\mathfrak{R}_{p,q}^{\Theta}}{q^2}}{\sum_{p=1}^{N^g}\sum_{q=1}^{N^r} \mathfrak{R}_{p,q}^{\Theta}} \quad (65)$$

VIII.2 long0_runs, long45_runs, long90_runs, long135_runs

These give large values for objects in which long runs, oriented at 0°, 45°, 90°, or 135°, dominate.

$$\text{long}\theta\_\text{runs} = \frac{\sum_{p=1}^{Ng} \sum_{q=1}^{Nr} q^2 R_{p,q}^{\Theta}}{\sum_{p=1}^{Ng} \sum_{q=1}^{Nr} R_{p,q}^{\Theta}} \qquad (66)$$

VIII.3 grey0_level, grey45_level, grey90_level, grey135_level

These features estimate grey level nonuniformity, taking on their lowest values when runs are equally distributed throughout the grey levels.

$$\text{grey}\theta\_\text{level} = \frac{\sum_{p=1}^{Ng}\left(\sum_{q=1}^{Nr} R_{p,q}^{\Theta}\right)^2}{\sum_{p=1}^{Ng} \sum_{q=1}^{Nr} R_{p,q}^{\Theta}} \qquad (67)$$

VIII.4 run0_length, run45_length, run90_length, run135_length

These features estimate the nonuniformity of the run lengths, taking on their lowest values when the runs are equally distributed throughout the lengths.

$$\text{run }\theta\_\text{length} = \frac{\sum_{q=1}^{Nr}\left(\sum_{p=1}^{Ng} R_{p,q}^{\Theta}\right)^2}{\sum_{p=1}^{Ng} \sum_{q=1}^{Nr} R_{p,q}^{\Theta}} \qquad (68)$$

VIII.5 run0_percent, run45_percent, run90_percent, run135_percent

These features are calculated as the ratio of the total number of possible runs to the object's area, having its lowest value for pictures with the most linear structure.

$$\text{run }\theta\_\text{percent} = \frac{\sum_{p=1}^{Ng} \sum_{q=1}^{Nr}\left(R_{p,q}^{\Theta}\right)}{A} \qquad (69)$$

where A is the object's area.

VIII.6 texture_orient

This feature estimates the dominant orientation of the object's linear texture.

$$\text{texture\_orient} = \frac{180}{\pi}\left(\frac{\pi}{2} + \arctan\left[\frac{(\lambda_1' - y_{pseudo\text{-}moment2})}{xy_{pseudo\text{-}cross\_moment2}}\right]\right) \qquad (70)$$

where $\lambda_1'$ is the maximal eigenvalue of the run length pseudo-second moment matrix (calculated in analogy to Section II.9). The run length pseudo-second moments are calculated as follows:

$$x_{pseudo\text{-}moment2} = \sum_{p=1}^{Ng} \sum_{q=1}^{Nr}\left[R_{p,q}^0 \sum_{l=1}^{q}(l^2 - l)\right] \qquad (71)$$

$$y_{pseudo\text{-}moment2} = \sum_{p=1}^{Ng} \sum_{q=1}^{Nr}\left[R_{p,q}^{90} \sum_{l=1}^{q}(l^2 - l)\right] \qquad (72)$$

$$xy_{pseudo\text{-}cross\_moment2} = \qquad (73)$$

$$\frac{\left(\sum_{p=1}^{Ng} \sum_{q=1}^{Nr}\left[R_{p,q}^{45} \cdot \sum_{l=1}^{q}(2l^2 - \sqrt{2}\,l)\right] - \sum_{p=1}^{Ng} \sum_{q=1}^{Nr}\left[R_{p,q}^{135} \cdot \sum_{l=1}^{q}(2l^2 - \sqrt{2}\,l)\right]\right)}{2\sqrt{2}}$$

Orientation is defined as it is for cell_orient, Section II.9, as the angle (measured in a clockwise sense) between the y axis and the dominant orientation of the image's linear structure.

VIII.7 size_txt_orient

This feature amplifies the texture orientation for long runs.

$$\text{size\_txt\_orient} = \frac{\lambda_1'}{\lambda_2'} \qquad (74)$$

where $\lambda_1', \lambda_2'$ are the maximal and minimal eigenvalues of the run_length pseudo-second moment matrix, defined in Section VIII.6.

Each of the above features are calculated for each in-focus object located in the image. Certain features are used by the classifier to separate artifacts from cell nuclei and to distinguish cells exhibiting MACs from normal cells. As indicated above, it is not possible to predict which features will be used to distinguish artifacts from cells or MAC cells from non-MAC cells, until the classifier has been completely trained and produces a binary decision tree or linear discriminant function.

In the present embodiment of the invention, it has been determined that thirty (30) of the above-described features appear more significant in separating artifacts from genuine nuclei and identifying cells with MACs. These primarily texture features are as follows:

| 30 preferred nuclear features |
| --- |
| 1) Area |
| 2) mean radius |
| 3) OD variance |
| 4) OD skewness |
| 5) range average |
| 6) OD maximum |
| 7) density of light spots |
| 8) low DNA area |
| 9) high DNA area |
| 10) low DNA amount |
| 11) high DNA amount |
| 12) high average distance |
| 13) mid/high average distance |
| 14) correlation |
| 15) homogeneity |
| 16) entropy |
| 17) fractal dimension |
| 18) DNA index |
| 19) run 0 percent |
| 20) run 45 percent |
| 21) run 90 percent |
| 22) run 135 percent |
| 23) grey level 0 |
| 24) grey level 45 |
| 25) grey level 90 |
| 25) grey level 135 |
| 27) run length 0 |
| 28) run length 45 |
| 29) run length 90 |
| 30) run length 135 |

Although these features have been found to have the best ability to differentiate between types of cells, other object types may be differentiated by the other features described above.

As indicated above, the ability of the system according to the present invention to distinguish cell nuclei from artifacts or cells that exhibit MACs from those that do not depends on the ability of the classifier to make distinctions based on the values of the features computed. For example, to separate cell nuclei from artifacts, the present invention may apply several different discriminant functions each of which is trained to identify particular types of objects. For example, the following discriminant function has been used in the presently preferred embodiment of the invention to separate intermediate cervical cells from small picnotic objects:

|  | cervical cells | picnotic |
| --- | --- | --- |
| max_radius | 4.56914 | 3.92899 |
| freq_low_fft | −.03624 | −.04714 |
| harmon03_fft | 1.29958 | 1.80412 |
| harmon04.fft | .85959 | 1.20653 |
| lowVSmed_DNA | 58.83394 | 61.84034 |
| energy | 6566.14355 | 6182.17139 |
| correlation | .56801 | .52911 |
| homogeneity | −920.05017 | −883.31567 |
| cl_shade | −67.317746 | −63.68423 |
| den_drk_spot | 916.69360 | 870.75739 |
| CONSTANT | −292.92908 | −269.42419 |

Another discriminant function that can separate cells from junk particles is:

|  | cells | junk |
| --- | --- | --- |
| eccentricity | 606.67365 | 574.82507 |
| compactness | 988.57196 | 1013.19745 |
| freq_low_fft | −2.57094 | −2.51594 |
| freq_high_fft | −28.93165 | −28.48727 |
| harmon02.fft | −31.30210 | −30.18383 |
| harmon03.fft | 14.40738 | 14.30784 |
| medDNAamnt | 39.28350 | 37.50647 |
| correlation | .27381 | .29397 |
| CONSTANT | −834.57800 | −836.19659 |

Yet a third discriminant function that can separate folded cells that should be ignored from suitable cells for analysis.

|  | normal interm | rejected objects |
| --- | --- | --- |
| sphericity | 709.66357 | 701.85864 |
| eccentricity | 456.09146 | 444.18469 |
| compactness | 1221.73840 | 1232.27441 |
| elongation | −391.76352 | −387.19376 |
| freq_high_fft | −37.89624 | −37.39510 |
| lowDNAamnt | −41.89951 | −39.42714 |
| low_den_obj | 1.40092 | 1.60374 |
| correlation | .26310 | .29536 |
| range_average | .06601 | .06029 |
| CONSTANT | −968.73628 | −971.18219 |

Obviously, the particular linear discriminant function produced by the classifier will depend on the type of classifier used and the training sets of cells. The above examples are given merely for purposes of illustration.

As can be seen, the present invention is a system that automatically detects malignancy-associated changes in a cell sample. By properly staining and imaging a cell sample, the features of each object found on the slide can be determined and used to provide an indication whether the patient from which the cell sample was obtained is normal or abnormal. In addition, MACs provide an indication of whether cancer treatment given is effective as well as if a cancer is in remission.

In another aspect, the present invention provides a system and method for automatically detecting diagnostic cells and cells having malignancy-associated changes. The system is an image cytometer based automated cytological specimen classifier useful for classifying cells within a cytological specimen (i.e., cell sample). In addition to the components of the image cytometer, which include a microscope for obtaining a view of the cytological specimen, a camera for creating an image of the view of the cell sample, an image digitizer for producing a digital representation of the image of the cells, and computer system for recording and analyzing the digital image and for controlling and interfacing these components, the automated classifier further includes a primary classifier for preliminarily classifying a cytological specimen, and a secondary classifier for classifying those portions of a cytological specimen initially classified by the primary classifier. Generally, the image cytometer captures images of cells of interest from a slide. The images are automatically classified into various cell subtypes, such as normal and abnormal epithelial cells or inflammatory cells. The classification can be achieved by using various classification schemes including linear and nonlinear classification methods that incorporate, for example, neural networks, binary decisions based upon directly calculated nuclear features, decision trees, decision webs, and discriminant functions. Several types of classifications can be performed.

Figure 11:
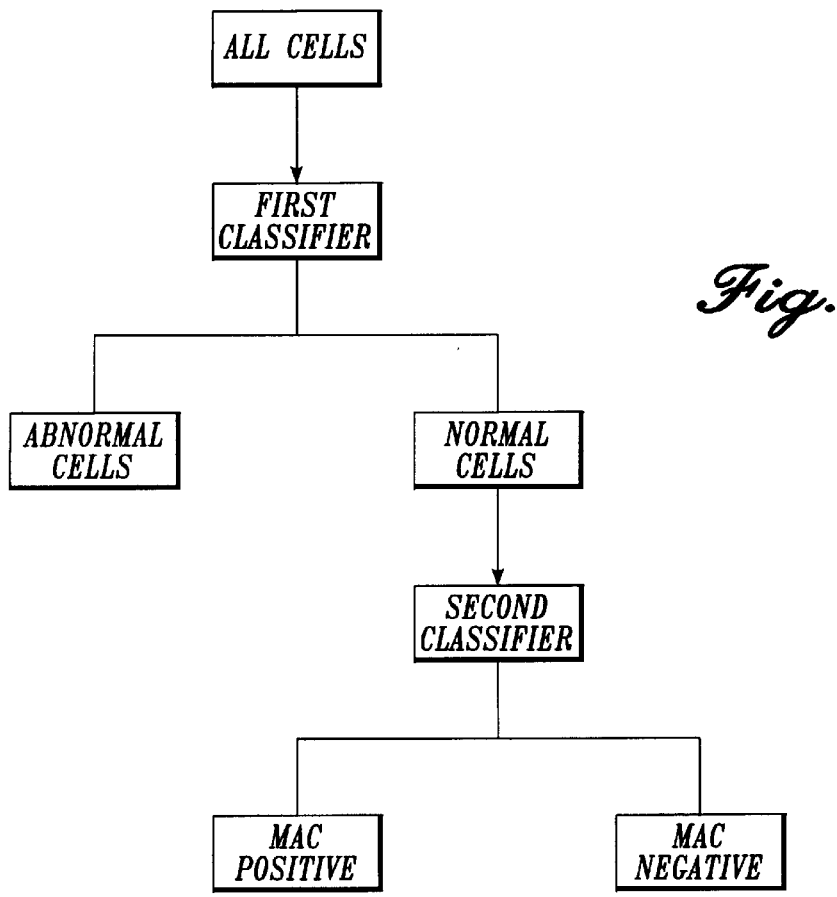
FIG. 11 is a diagrammatic illustration of an automated classifier system of the present invention.

In a preferred embodiment of the present invention, the primary classifier distinguishes and selects epithelial cells from among the cells of the cell sample, and the secondary classifier indicates whether the selected epithelial cells are normal (i.e., MAC negative) or have malignancy-associated changes (i.e., MAC positive). Thus, applying the principles generally described above, the first automated classifier screens a cell sample for epithelial cells, whether normal or diagnostic, and then the second classifier identifies the normal cells as normal and MAC-negative or normal and MAC-positive. The overall system of the present invention is schematically represented in FIG. 11. It will be appreciated that although the system of the present invention includes a first (i.e., primary) and a second (i.e., secondary) classifier as depicted in FIG. 11, the classifications obtained by the present system can be achieved by a single classifier that sequentially performs the primary and secondary classifications further described below.

As used herein, the term "diagnostic cell" refers to a visually apparent cancerous (i.e., malignant) cell or a pre-cancerous (i.e., pre-malignant) cell. The term "cancerous cell" refers to an invasive cancerous cell, and the term "pre-cancerous cell" refers to a pre-invasive cancerous cell. Generally, only a fraction of pre-invasive cancerous cells mature to invasive cancerous cells. The term "malignancy-associated change" or "MAC" refers to subvisual or nearly subvisual changes to the chromatin arrangement of visually normal nuclei, the changes being correlated to the presence of a tumor in a patient.

The system includes classifiers that can work together to determine whether a particular cell sample includes diagnostic cells and cells having malignancy-associated changes. As described above, a classifier is a computer program that analyzes an object based on certain feature values. The automated classifier system of the present invention includes a primary classifier, which performs a basic screening function, and selects normal epithelial cells. A secondary classifier classifies the epithelial cells as either normal and having malignancy-associated changes or normal and not exhibiting malignancy-associated changes. As noted above, while the automated system of the present invention preferably includes a primary and secondary classifier, a single classifier can be used to sequentially obtain the classifications achieved by the present invention. The software packages used to generate classification functions based on statistical methods are generally commercially available. Statistical classifiers useful in the present invention have been constructed as generally described above and shown in FIGS. 8 and 9.

The automated classifier of this invention preferably includes classifiers that utilize binary decisions based on directly calculated nuclear features in performance of their classification function. While the classifier can be constructed to include a large number of feature values, including the morphological features, photometric features, discrete texture features, Markovian texture features, non-Markovian texture features, fractal texture features, and run length texture features, it has been determined that of the features described above, 33 appear more significant in identifying epithelial cells and identifying diagnostic cells and cells having malignancy-associated changes. These features include:

1) area
2) mean radius
3) OD variance
4) OD skewness
5) range average
6) OD maximum
7) density of light spots
8) low DNA area
9) high DNA area
10) low DNA amount
11) high DNA amount
12) high average distance
13) mid/high average distance
14) correlation
15) homogeneity
16) entropy
17) fractal dimension
18) DNA index
19) run 0 percent
20) run 45 percent
21) run 90 percent
22) run 135 percent
23) grey level 0
24) grey level 45
25) grey level 90
25) grey level 135
27) run length 0
28) run length 45
29) run length 90
30) run length 135
31) harmonic 4
32) harmonic 5
33) harmonic 6

Although these features have been determined to have the best ability to differentiate between types of cells, other object types may be differentiated by other features.

Figure 12:
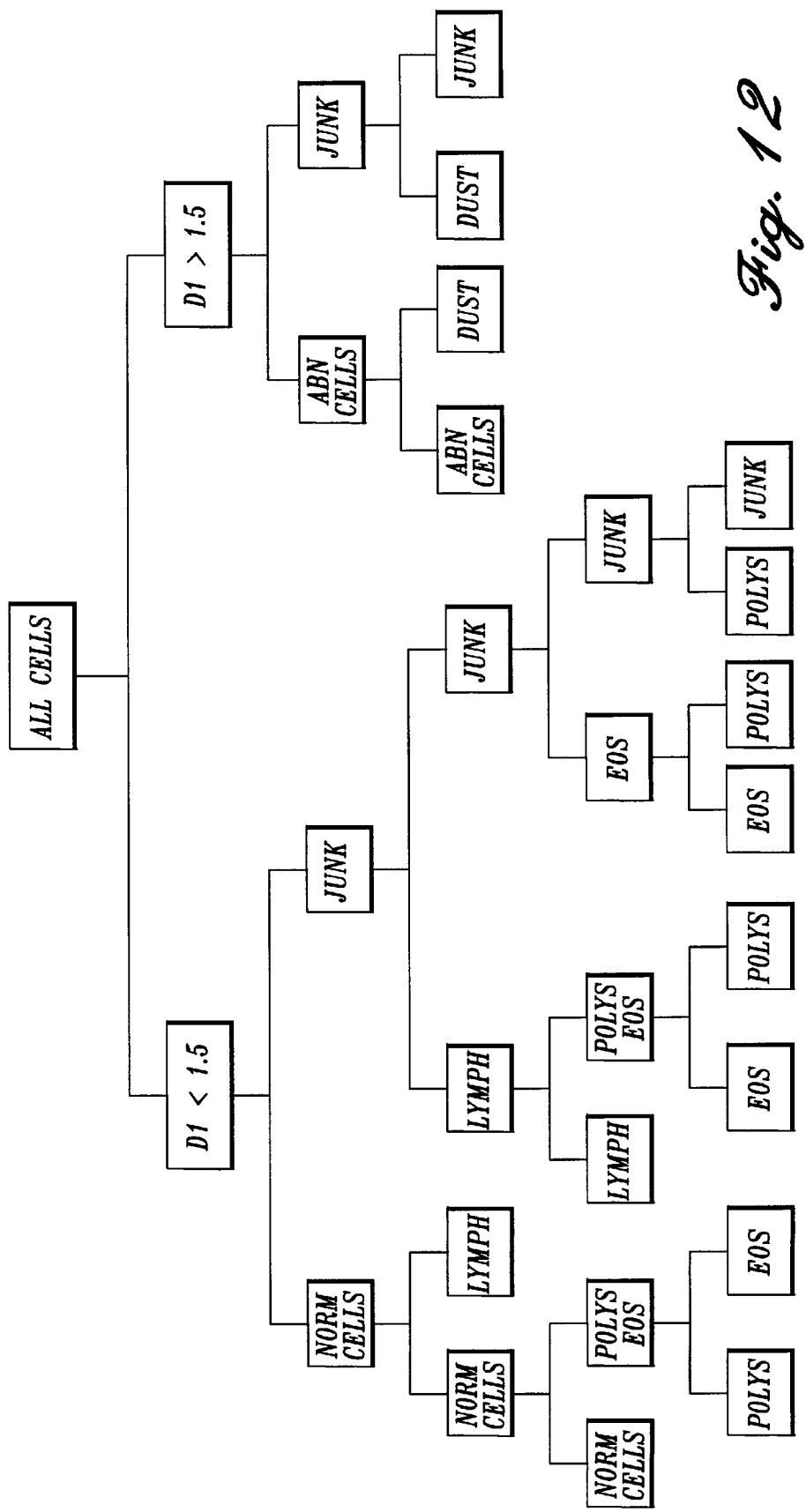
FIG. 12 is a flow chart of the binary decision tree employed by the primary classifier to classify epithelial cells in a cell sample, where "DI" refers to DNA index (normal= 1.0), "norm cells" refers to normal cells, "junk" refers to debris, "lymph" refers to lymphocytes, "abn cells" refers to abnormal epithelial cells, "dust" refers to pulmonary alveolar macrophages, "polys" refers to polymorphonuclear neutrophilic leukocytes, and "eos" refers to polymorphonuclear eosinophilic leukocytes.

The primary classifier functions to subtype cells into three classes: (1) epithelial cells including diagnostic cells and cells that may contain malignancy-associated changes; (2) inflammatory cells; and (3) junk. The primary classifier affects cell-by-cell classification through a binary decision tree incorporating a selection of feature values as shown in FIG. 12. In a preferred embodiment, the primary classifier performs its classification function utilizing the 33 features noted above.

As indicated above, the ability of the system of the present invention to distinguish cell nuclei from artifacts, epithelial cells from other cell types, and cells having malignancy-associated changes from other normal epithelial cells depends on the ability of the classifier to make distinctions based on the values of the features computed. For example, to distinguish normal epithelial cells from abnormal epithelial cells (i.e., diagnostic cells), the present invention may apply several different discriminant functions, each of which is trained to identify particular types of objects. For example, the following discriminant function has been used in one presently preferred embodiment of the invention to distinguish normal epithelial cells from abnormal cells:

| FEATURE | Normal | Cancer |
| --- | --- | --- |
| 2 harmon05 | 199.62447 | 223.06030 |
| 3 freqmac2 | 34.19107 | 50.18366 |
| CONSTANT | −51.21967 | −65.70574 |

Although the above functions have been successful in distinguishing normal epithelial cells from abnormal cells, those skilled in the art will recognize that the exact weights used in the functions will depend on the type of classifier used and the training sets of cells. The above example is given merely for the purpose of illustration.

Figure 13:
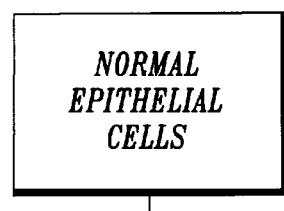
FIG. 13 is a flow chart of the binary decision tree employed by the secondary classifier to classify cells having malignancy-associated changes (i.e., MAC positive cells) among epithelial cells in a cell sample.

The secondary classifier classifies the epithelial cells in the cell sample selected by the primary classifier and also uses a binary decision tree and feature values in performance of its classification function. The secondary classifier, which can be considered as a slide-by-slide classifier, analyzes the epithelial cells classified by the primary classifier and classifies those cells as normal and MAC-negative or normal and MAC-positive. The secondary classifier thus distinguishes normal epithelial cells having malignancy-associated changes (i.e., MAC positive) from normal epithelial cells that do not exhibit malignancy-associated changes (i.e., MAC negative). As with the primary classifier, the secondary classifier is constructed to distinguish cells based on a set of preferred nuclear features. In a preferred embodiment, the secondary classifier performs its classification function utilizing the following features:

1) area
2) density of light spots
3) low DNA area
4) high DNA area
5) low DNA amount
6) high DNA amount
7) correlation
8) homogeneity
9) entropy
10) fractal dimension
11) DNA index
12) OD maximum
13) medium DNA amount The operation of the secondary classifier is schematically shown in FIG. 13.

The feature sets used by each classifier are developed from discriminant functions analyzing quantitative features of cell nuclei and, preferably, include a minimum number of features. Ideally, the selection of a minimum number of optimal nuclear features results in an efficient and robust classifier. That is, a classifier is preferably both efficient in accurately classifying a cell or a cell type, and robust in reliably classifying a variety of cell and slide preparations.

The ability of the system of the present invention to distinguish cells having malignancy-associated changes from epithelial cells that do not exhibit such changes depends on the ability of the classifier to make distinctions based on the values of the features computed. To distinguish cells having malignancy-associated changes from cells that do not, the present invention may apply several different discriminant functions, each of which is trained to identify particular types of objects. For example, the following discriminant function has been used in the presently preferred embodiment of the invention to distinguish cells having malignancy-associated changes from normal epithelial cells that do not exhibit malignancy-associated changes:

| FEATURE | MAC-negative | MAC-positive |
| --- | --- | --- |
| 30 harmon03_fft | 3.52279 | 3.82334 |
| 93 cl_shade | 0.99720 | −1.09342 |
| 96 den_drk_spot | 168.27394 | 189.80289 |
| 105 fractal2_area | 0.00372 | 0.00056 |
| CONSTANT | −63.66887 | −67.90617 |

Although the above functions have been successful in distinguishing normal MAC-negative cells from normal MAC-negative cells, those skilled in the art will recognize that the exact weights used in the functions will depend on the type of classifier used and the training sets of cells. The above example is given merely for the purpose of illustration.

The selection of features for construction of a classifier can often depend on the method of cell fixation and nuclear staining. Thus, the selection of a feature set for a particular cell preparation will depend upon the method by which the cells were fixed and stained. While some feature sets are sufficiently robust to be useful in diagnosing a number of conditions, it has been found that malignancy-associated changes are quite sensitive to fixation method. For example, formalin fixation, a commonly used fixation for tissue preparations, provides fixed cells that are not efficiently classified by the preferred embodiment of the automated classifier system of the present invention. However, using the principles of the present invention, a classifier could be constructed to efficiently and robustly classify such fixed cells. In the practice of the present invention, Saccamanno fixation and its variants, and Bohm-Sprenger fixation and its variants are preferred methods of fixation.

After a cell sample is fixed, the sample is then stained with a nuclear stain to identify cell nuclei within the sample. Preferably, the cellular DNA staining is a quantitative and stoichiometric staining of the DNA. Preferred stoichiometric DNA stains include Feulgen stains, such as thionine and para-rosanaline; Rousmouski stains, such as Wright stain, May-Grunwald-Geimsa stain, and Hematoxylin; and Methyl Green. In a preferred embodiment, the Feulgen stain is thionin. Other stains including qualitative stains, such as Hematoxylin and Eosin, can also be used. Representative fixation and staining procedures are described in Example 1 below.

The automated classifier of the system and method of the present invention are used for classifying cells obtained from a cytological specimen. In general, the system and method of the present invention are useful for classifying a wide variety of cytological specimens. For example, the present invention is useful in the classification of cytological specimens in the form of cervical smears in connection with a Pap test. Histological specimens including tissue sections, such as are generally taken from a tissue obtained during a tumor biopsy or during surgical removal of a tumor, may also be classified. The system and method of the present invention are particularly well suited for the classification of bronchial specimens. As used herein, the term "bronchial specimen" refers to both tissue acquired during bronchoscopy or surgery, and to cytological specimens that originated in whole or in part from the bronchial epithelium whether acquired by brushing, washing, or sputum cytology. The system and method of the present invention have been found to be effective in detecting diagnostic cells and cells having malignancy-associated changes in cell samples derived from lung sputum. A representative method for the collection of lung sputum is described in Example 2.

The system and method of the present invention are particularly well-suited for the classification of epithelial cells and, consequently, useful in the diagnosis and monitoring of various epithelial cancers including lung cancer, breast cancer, prostate cancer, cancers of the gastrointestinal tract, and skin cancer, among other.

The method for detecting epithelial cells in a cell sample generally includes the steps of: (1) obtaining a cell sample; (2) staining the sample to identify cell nuclei within the sample; (3) obtaining an image of the cell sample with a digital microscope having a digital CCD camera and a programmable slide stage such as described above; (4) focusing the image; (5) identifying objects in the image; (6) calculating a set of feature values for each object identified; and (7) analyzing the feature values to determine whether each object is an epithelial cell. As described above for the primary classifier, the step of analyzing the feature values to determine whether each object is an epithelial cell includes the use of a binary decision tree that considers the nuclear features noted above.

The method for detecting diagnostic cells and cells having malignancy-associated changes generally includes the same steps as described above for the method for detecting epithelial cells, however, the steps of calculating a set of feature values and analyzing the feature values rely on the secondary classifier as described above to determine whether each object is a normal epithelial cell having a malignancy-associated change or a normal epithelial cell that is not exhibiting a malignancy-associated change. As with the secondary classifier, the analyzing step includes the use of a binary decision tree that utilizes nuclear features to classify the cells.

Both of the above-described methods are applicable to the analysis of a wide variety of cytological specimens including bronchial specimens such as lung sputum.

The present invention also provides a method for detecting diagnostic cells and cells having malignancy-associated changes and further predicting whether a patient will develop cancer. Generally, the method detects pre-invasive cancerous cells and predicts whether the patient will develop invasive cancer. The method includes the steps of obtaining a sample of cells from the patient, determining whether the cells in the sample include either diagnostic cells or cells having malignancy-associated changes by first staining the nuclei of the cells in the sample to obtain an image of those cells with a microscope and recording the image in a computer system; and secondly, analyzing the stored image of the cells to identify the nuclei, and then computing a set of feature values for each nucleus found in the sample and from those feature values determine whether the nucleus is the nucleus of a normal cell or a cell having a malignancy-associated change. After such a determination, the total number of cells having malignancy-associated changes is determined and from that number a predication of whether the patient will develop cancer can be made. The prediction is based upon threshold values for diagnostic cells and cells having malignancy-associated changes similar to the predictive method described above for MAC-positive cells.

The following examples are provided for the purposes of illustration, and not limitation.

EXAMPLES

Example 1

Representative Procedure for Cell Fixing and Cellular DNA Staining

In this example, a representative procedure for fixing cells and staining cellular DNA with thionin is described. The reagents used in the DNA staining procedure, including methanol and t-butanol solutions of thionin, and fixative and rinse solutions, are prepared as described below.

Stain Reagent Preparations

A. Methanolic Feulgen Staining Solution

Thionin/Methonol Staining Solution

1. Add 0.5 g thionin (Aldrich Chemical Co., Milwaukee, Wis.) and 0.5 g sodium metabisulfite to a 500 ml glass bottle with a stirring bar.
2. Add 200 ml methanol. Mix well.
3. Add 250 ml distilled water.
4. Add 50 ml 1N hydrochloric acid and cap the bottle.
5. Stir stain solution for one hour. Protect solution from light by wrapping the bottle with aluminum foil. Do not refrigerate.
6. Filter stain solution through filter paper (No. 1 grade) in a fume hood immediately prior to use.

B. Conventional Feulgen Staining Solution

Thionin/t-Butanin Staining Solution

1. Add 0.5 g thionin to 435 ml distilled water in a 2000 ml Erlenmeyer flask.
2. Heat solution to boiling for about 5 minutes and then allow to cool to about room temperature.
3. Add 435 ml t-butanol. (If necessary, melt the t-butanol in a waterbath. The melting point of t-butanol is 25–26° C. and therefore is a solid at temperatures below about 25° C.).
4. Add 130 ml 1N aqueous hydrochloric acid.
5. Add 8.7 g sodium metabisulfite.
6. Add stirring bar and seal container with Parafilm M.
7. Stir stain solution for at least 1 hour. Protect from light and do not refrigerate.
8. Filter stain solution through filter paper (No. 1 grade) in a fume hood just prior to use.

Other Reagent Preparations

Bohm-Sprenger Fixative

1. Combine 320 ml methanol and 60 ml aqueous formaldehyde (37%) in a 500 ml glass bottle.
2. Add 20 ml glacial acetic acid.
3. Mix well and seal with Parafilm M.

Rinse Solution

1. Dissolve 7.5 g sodium metabisulfite in 1425 ml distilled water in a 2000 ml Erlenmeyer flask.
2. Add 75 ml 1N aqueous hydrochloric acid.
3. Add stirring bar and stir until dissolved. Seal flask with Parafilm M.

1% Acid Alcohol

1. Mix 280 ml of absolute ethanol and 120 ml distilled water.
2. Add 4 ml concentrated hydrochloric acid.
3. Mix well.

The reagents prepared as described above were then used to fix cells and stain cellular DNA by the following method. Preparations of cells of interest (e.g., cells from uterine cervix samples or lung sputum samples), including conventional smears and monolayer preparations, may be used in the method. In the method, cells are generally deposited on a microscope slide for staining.

Fixing and Staining Procedure

1. Deposit cells on a microscope slide.
2. Fix cells by immersing slide in Bohm-Sprenger fixative: 30–60 minutes.
3. Rinse slide in distilled water: 1 minute, agitate.
4. Hydrolyze cellular DNA by immersing slide in 5N hydrochloric acid: 60 minutes at room temperature.
5. Rinse slides in distilled water: 15 dips, agitate.
6. Stain cells by applying freshly filtered thionin stain solution: 75 minutes.
7. Wash slides in distilled water: 6 changes, 20 dips each.
8. Rinse slides in freshly prepared rinse solution: 3 changes: 30 seconds for the first two rinses, 5 minutes for the last rinse.
9. Rinse slides in distilled water: 3 changes, 20 dips each.
10. For mucoidal samples only: Optionally rinse slides in 1% acid alcohol: 2 minutes.
11. Rinse slides in distilled water: 3 changes, 20 dips each.
12. Dehydrate cells by sequentially immersing the slides in 50%, 75% aqueous ethanol and two changes of 100% ethanol: 1 minute each.

13. Clear slides by immersing in xylene: 5 minutes.
14. Mount coverslips on slides.
15. Identify slides with barcode labels if desired.

Example 2

Representative Procedure for Collecting Lung Sputum

In this example, a representative procedure for collecting lung sputum is described. Generally, lung sputum may be collected by either an induction or pooled method.

Induction Method

Sputum induction using sterile water or saline solution increases both the mobility and quantity of sputum available for examination. Preferably, the subject first clears his/her throat and rinses the mouth thoroughly, and possibly brushes the teeth to reduce background debris that might influence the results. The subject then performs the three deep-breath/three deep-cough technique as described below:

1. A nebulizer with disposal mouthpiece is placed in the subject's mouth.
2. A disposable nose clip is applied to the subject's nose.
3. A timer is set for one minute.
4. The subject inhales and exhales the nebulizer mist through the mouth for one minute breathing normally.
5. The subject performs the first deep breath by inhaling the maximum inspiratory breath of mist through the mouthpiece, holding for five seconds, and forcefully exhaling into a tissue paper.
6. The subject performs the second deep breath by repeating step 5.
7. The subject performs the third deep breath by inhaling the maximum inspiratory breath of mist through the mouthpiece, holding for five seconds, covering the mouth with tissue, coughing deeply, and spitting sputum into the sputum collection jar containing 30 ml of fixative (prepared as described in Example 3).
8. The subject repeats steps 3–7 five times.

Three-Day Pooling Method

In the three-day pooling method, the subject collects an early morning sputum sample on three or more subsequent mornings according to the three-day pooling method outlined below:

1. The subject clears his/her throat and rinses the mouth thoroughly, and possibly brushes the teeth to reduce background debris that might influence the results.
2. The subject produces the sputum sample and spits it into the sample collection jar containing 30 ml of fixative (prepared as described in Example 3).
3. The subject refrigerates the specimen collected in jar overnight.
4. The subject repeats steps 1–3 for two or more subsequent mornings.

Example 3

Representative Fixation Solutions

Fixation is one of the most critical steps in the image cytometry and classification of Feulgen stained cells. It has been determined that the fixative chemistry influences the staining results and, consequently, the cell classification. Several fixatives have been investigated for their suitability and an ethanol and polyethylene glycol mixture has been identified as a preferred fixative.

The standard fixative, a 50% aqueous ethanolic solution that includes 1–2% polyethylene glycol by volume, is used in the sample collection jars to preserve and fix the sputum sample until cytology sample preparation. The standard fixative is prepared by adding 384 ml of fixative concentrate (SEDFIX, SurgiPath Company) to a four liter container followed by the addition of 1700 ml of distilled water and 1700 ml of 95% ethanol.

To prepare the preferred fixative, the standard fixative is modified by the addition of dithiothreitol (DTT). Independent studies indicate that DTT breaks up mucous and increases the yield of diagnostic cells without adversely affecting morphology when low concentrations are used. DTT has also been discovered to reduce the background staining of the specimens. The DTT fixative is used during sample preparation and provides a post-fixation method to break up mucous in the sputum sample. The DTT fixative solution is prepared by adding 0.4 grams DTT to four liters of the standard fixative prepared as described above.

Example 4

Representative Procedure for Preparing a Sputum Sample for Classification

In this example, a representative procedure for preparing a sputum sample for classification by the system and method of the present invention is described.

A sputum sample obtained as described in Example 2 above is prepared for classification as outlined below:

1. Transfer the specimen to a centrifuge tube and rinse the original specimen container with a few milliliters of standard fixative (prepared as described in Example 3), transferring the rinse to the centrifuge tube.
2. Centrifuge at 1000 g for 10 minutes.
3. Discard the supernatant.
4. Resuspend the cell pellet in 30 ml of DTT fixative (prepared as described in Example 3). Vortex to mix and allow to stand for 60 minutes. Vortex after 30 minutes to ensure mixing.
5. During this time and centrifuge times, prepare 6 to 10 high adhesion microscope slides (3–5 pairs) for analysis.
6. Washing step. Centrifuge at 1000 g for 10 minutes. After centrifuging, discard the supernatant, and resuspend by vortexing the cell pellet in 30 ml of standard fixative. Centrifuge again at 1000 g for 10 minutes. Discard the supernatant from the pellet without disturbing the pellet.
7. To the cell pellet, add enough standard fixative to produce 6–10 drops.
8. Vortex each tube until homogeneous to resuspend the cells.
9. Using a 1 ml disposable transfer pipette, place one drop of mixed cell suspension in the center of a high adhesion microscope slide.
10. Take the paired slide and place face down on the first slide and gently press together, then draw gently across in a pulling motion. The object is to achieve a smooth monolayer of cells. Do not allow the specimen to collect at the end of the slide.
11. Air-dry slides completely to reduce the risk of cross-contamination prior to analysis.

Slides as prepared as described are then stained by a method such as described in Example 1 above.

After staining, the slide is coverslipped. Coverslipping involves placing a mounting medium (e.g., xylene mounting media such as Cytoseal available from VWR Scientific or Permount available from Fisher Scientific; or an immersion oil), which is usually soluble in xylenes, onto the specimen as a drop or two. A thin piece of glass, the coverslip, is then placed on top of the slide-specimen-mounting media. The mounting media spreads out between the slide and coverslip. Air bubbles must be avoided. The mounting media is manufactured such that it matches the refractive index of the glass used in the slide and coverslip. This combination is allowed to air-dry at room temperature, usually overnight, but at least long enough for the mounting media to solidify. This time may be as short as one hour. For slides that use an immersion oil as mounting media, no solidification occurs. Slides prepared as described above are ready for analysis and classification by the automated classifier system of the present invention.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for detecting epithelial cells in a cell sample, comprising the steps of:
   a. obtaining a cell sample;
   b. fixing the cells of the cell sample;
   c. staining the cells to identify cell nuclei in the cell sample;
   d. illuminating the sample and obtaining an image of the sample with a microscope and a digital camera;
   e. compensating the image for variations in background illumination;
   f. analyzing the image to detect objects of interest;
   g. determining a focus setting for each object of interest and obtaining an image of each object of interest at its determined focus setting;
   h. calculating an edge that bounds each object of interest;
   i. calculating a set of feature values for each object of interest; and
   j. providing the set of feature values to a classifier that identifies epithelial cells in the objects of interest.

2. The method of claim 1, wherein the features used to identify epithelial cells in the cell sample comprise features selected from the group consisting of area, mean radius, OD variance, OD skewness, range average, OD maximum, density of light spots, high DNA area, high DNA area, low DNA amount, high DNA amount, high average distance, mid/high average distance, correlation, homogeneity, entropy, fractal dimension, DNA index, run 0 percent, run 45 percent, run 90 percent, run 135 percent, grey level 0, grey level 45, grey level 90, grey level 135, run length 0, run length 45, run length 90, run length 135, harmonic 4, harmonic 5, and harmonic 6.

3. The method of claim 1, wherein the classifier identifies epithelial cells using a discriminant function, wherein the discriminant function uses features selected from the group consisting of harmon05 and freqmac2.

4. The method of claim 1, wherein the cell sample is a human lung specimen.

5. The method of claim 1, wherein staining the sample to identify cell nuclei comprises staining with a stoichiometric DNA stain.

6. The method of claim 5, wherein the stoichiometric DNA stain is selected from the group consisting of a Feulgen stain, a Romanowski stain, May-Grunwald-Giemsa stain, and Methyl Green.

7. The method of claim 5, wherein the stoichiometric DNA stain is thionin.

8. A method for detecting a diagnostic cell in a cell sample, comprising the steps of:
   a. obtaining a cell sample;
   b. fixing the cells of the cell sample;
   c. staining the cells to identify cell nuclei in the cell sample;
   d. illuminating the sample and obtaining an image of the sample with a microscope and a digital camera;
   e. compensating the image for variations in background illumination;
   f. analyzing the image to detect objects of interest;
   g. determining a focus setting for each object of interest and obtaining an image of each object of interest at its determined focus setting;
   h. calculating an edge that bounds each object of interest;
   i. calculating a set of feature values for each object of interest; and
   j. providing the set of feature values to a classifier that identifies a diagnostic cell in the objects of interest.

9. The method of claim 8, wherein the features used to identify a diagnostic cell comprise features selected from the group consisting of area, mean radius, OD variance, OD skewness, range average, OD maximum, density of light spots, low DNA area, high DNA area, low DNA amount, high DNA amount, high average distance, mid/high average distance, correlation, homogeneity, entropy, fractal dimension, DNA index, run 0 percent, run 45 percent, run 90 percent, run 135 percent, grey level 0, grey level 45, grey level 90, grey level 135, run length 0, run length 45, run length 90, run length 135, harmonic 4, harmonic 5, and harmonic 6.

10. The method of claim 8, wherein the features used to identify a diagnostic cell comprise features selected from the group consisting of area, density of light spots, low DNA area, high DNA area, low DNA amount, high DNA amount, correlation, homogeneity, entropy, fractal dimension, DNA index, OD maximum, and medium DNA amount.

11. The method of claim 8, wherein the classifier identifies a diagnostic cell in a cell sample using a discriminant function, wherein the discriminant function uses features selected from the group consisting of harmon03 fft, cl shade, den drk spot, and fractal2 area.

12. The method of claim 8, wherein the diagnostic cell is diagnostic of cancer.

13. The method of claim 10, wherein the diagnostic cell is a preinvasive cancerous cell.

14. The method of claim 10, wherein the diagnostic cell is an invasive cancerous cell.

15. A method for screening a patient for cancer, comprising the steps of:
   a. obtaining a cell sample;
   b. fixing the cells of the cell sample;
   c. staining the cells to identify cell nuclei in the cell sample;
   d. illuminating the sample and obtaining an image of the sample with a microscope and a digital camera;
   e. compensating the image for variations in background illumination;
   f. analyzing the image to detect objects of interest;
   g. determining a focus setting for each object of interest and obtaining an image of each object of interest at its determined focus setting;
   h. calculating an edge that bounds each object of interest;
   i. calculating a set of feature values for each object of interest;
   j. providing the set of feature values to a first classifier that identifies epithelial cells in the objects of interest; and k. providing the set of feature values calculated for the objects of interest that were identified as epithelial cells to a second classifier that identifies whether the epithelial cells include diagnostic cells in the objects of interest.

16. A method for determining whether a patient will develop invasive cancer, comprising the steps of:

obtaining a cell sample from the patient;

determining whether the cells in the sample include a diagnostic cell by:

(1) staining the nuclei of the cells in the sample;

(2) obtaining an image of the cells with a digital microscope and recording the image in a computer system;

(3) analyzing the stored image of the cells to identify epithelial cells;

(4) computing a set of feature values for the epithelial cells identified in the sample and from the feature values determining whether the epithelial cells include a diagnostic cell; and determining a total number of diagnostic cells in the cell sample and from the total number predicting whether the patient will develop invasive cancer.

17. The method of claim 16, wherein the invasive cancer is an epithelial cancer.

18. The method of claim 17, wherein the epithelial cancer is selected from the group consisting of lung cancer, breast cancer, prostate cancer, skin cancer, and cancer of the gastrointestinal tract.

19. An automated cytological specimen classifier for identifying diagnostic cells, comprising:

a microscope for obtaining a view of a cytological specimen located on a slide;

a camera for creating an image of the view;

an image digitizer for producing a digital representation of the image; and a computer system for controlling and interfacing the microscope, camera, and image digitizer, wherein the computer system analyzes the digital representation of the image to locate one or more objects of interest and calculates a set of feature values for each object of interest, the computer system further including:

a first classifier for identifying normal and abnormal epithelial cells in the digital representation of the image based on a first set of feature values computed for the object of interest; and a second classifier for identifying normal epithelial cells as diagnostic cells based on a second set of feature values computed for the objects of interest that were identified as normal epithelial cells.

20. The automated classifier of claim 19 wherein the microscope is a digital microscope.

21. The automated classifier of claim 19 wherein the camera is a CCD camera.

22. The automated classifier of claim 19 wherein the first and second set of feature values are selected from the group consisting of area, mean radius, OD variance, OD skewness, range average, OD maximum, density of light spots, low DNA area, high DNA area, low DNA amount, high DNA amount, high average distance, mid/high average distance, correlation, homogeneity, entropy, fractal dimension, DNA index, run 0 percent, run 45 percent, run 90 percent, run 135 percent, grey level 0, grey level 45, grey level 90, grey level 135, run length 0, run length 45, run length 90, run length 135, harmonic 4, harmonic 5, and harmonic 6.

23. The automated classifier of claim 19 wherein the second detectable features comprise features selected from the group consisting of area, density of light spots, low DNA area, high DNA area, low DNA amount, high DNA amount, correlation, homogeneity, entropy, fractal dimension, DNA index, OD maximum, and medium DNA amount.

* * * * *

UNITED STATES PATENT AND TRADEMARK OFFICE
CERTIFICATE OF CORRECTION

PATENT NO. : 6,026,174  
DATED : February 15, 2000  
INVENTOR(S) : B. Palcic et al.

Page 1 of 1

It is certified that error appears in the above-identified patent and that said Letters Patent is hereby corrected as shown below:

Title page,
Attorney, Agent or Firm, "pllc" should read -- PLLC --

Item [73],
Assignee, "AccuMed International, Inc., Chicago, Ill." should read
-- Oncometrics Imaging Corp., Vancouver, B.C., Canada --

Item [56],
References Cited, (FOREIGN PATENT REFERENCES, Item 1) delete the line beginning: "0 595 506 A2  4/1994  European…"

Signed and Sealed this

Twenty-fifth Day of December, 2001

Attest:

JAMES E. ROGAN
Attesting Officer    *Director of the United States Patent and Trademark Office*

UNITED STATES PATENT AND TRADEMARK OFFICE
CERTIFICATE OF CORRECTION

PATENT NO. : 6,026,174        Page 1 of 1
DATED     : February 15, 2000
INVENTOR(S) : B. Palcic et al.

It is certified that error appears in the above-identified patent and that said Letters Patent is hereby corrected as shown below:

<u>Title page,</u>
Attorney, Agent or Firm, "pllc" should read -- PLLC --

<u>Item [73],</u>
Assignee, "AccuMed International, Inc., Chicago, Ill." should read
-- Oncometrics Imaging Corp., Vancouver, B.C., Canada --

<u>Item [56],</u>
References Cited, (FOREIGN PATENT REFERENCES, Item 1) delete the line beginning: "0 595 506 A2  4/1994  European..."

Signed and Sealed this

Eighth Day of January, 2001

Attest:

Attesting Officer

JAMES E. ROGAN
Director of the United States Patent and Trademark Office